US011065344B2

(12) United States Patent
Alsaiari et al.

(10) Patent No.: US 11,065,344 B2
(45) Date of Patent: Jul. 20, 2021

(54) NANOCLUSTER CAPPED MESOPOROUS NANOPARTICLES, METHODS OF MAKING AND USE

(71) Applicant: King Abdullah University of Science and Technology, Thuwal (SA)

(72) Inventors: Shahad Alsaiari, Thuwal (SA); Mohamed Amen Hammami, Thuwal (SA); Niveen M. Khashab, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 6 days.

(21) Appl. No.: 16/338,933

(22) PCT Filed: Oct. 2, 2017

(86) PCT No.: PCT/IB2017/056072
§ 371 (c)(1),
(2) Date: Apr. 2, 2019

(87) PCT Pub. No.: WO2018/065884
PCT Pub. Date: Apr. 12, 2018

(65) Prior Publication Data
US 2020/0046849 A1 Feb. 13, 2020

Related U.S. Application Data

(60) Provisional application No. 62/403,391, filed on Oct. 3, 2016.

(51) Int. Cl.
*A61K 47/69* (2017.01)
*A61K 47/62* (2017.01)
*A01N 25/26* (2006.01)
*A61K 31/7036* (2006.01)
*G01N 33/569* (2006.01)

(52) U.S. Cl.
CPC .......... *A61K 47/6929* (2017.08); *A01N 25/26* (2013.01); *A61K 31/7036* (2013.01); *A61K 47/62* (2017.08); *A61K 47/6923* (2017.08); *G01N 33/56955* (2013.01)

(58) Field of Classification Search
CPC . A61K 47/6929; A61K 47/62; A61K 47/6923
See application file for complete search history.

(56) References Cited

U.S. PATENT DOCUMENTS 8,080,285 B2   12/2011   Beigbeder et al.
8,808,724 B2    8/2014   Cichocki et al.

FOREIGN PATENT DOCUMENTS

WO   2014041508 A1   3/2014
WO   2015107476 A1   7/2015

OTHER PUBLICATIONS

Croissant, J.G. et al. "Protein-gold clusters-capped mesoporous silica nanoparticles for high drug loading, autonomous gemcitabine/doxorubicin co-delivery, and in-vivo tumor imaging" Journal of Controlled Release 229 (2016) 183-191 (Year: 2016).*
Croissant, J.G. "Protein-gold clusters-capped mesoporous silica nanoparticles for high drug loading, autonomous gemcitabine/doxorubicin co-delivery, and in-vivo tumor imaging" Journal of Controlled Release 229 (2016) 183-191 (Year: 2016).*
Doxorubin (http://chemocare.com/chemotherapy/drug-info/doxorubicin.aspx) pp. 1-6, accessed Oct. 1, 2020 (Year: 2020).*
Drugs.com (https://www.drugs.com/cdi/kanamycin.html) pp. 1-4, available Sep. 4, 2014 (Year: 2014).*
Finley, et al., "The Prevalence of Phenotypic Silver Resistance in Clinical Isolates", Wounds, vol. 25, No. 4, Apr. 2013, pp. 84-88.
Pulizzi, et al., "Nanotechnology in Food: Silver-Lined Packaging", Nature Nanotechnology, Feb. 2016, 113.
Song, et al., "Silica Nanopollens Enhance Adhesion for Long-Term Bacterial Inhibition", J. Am. Chem. Soc., vol. 138, No. 20, May 3, 2016, pp. 6455-6462.
Notification of Transmittal of the International Search Report and the Written Opinion of the International Searching Authority, or the Declaration for PCT/IB2017/056072 dated Dec. 14, 2017.
Croissant, et al., "protein-gold clusters-capped mesoporous silica nanoparticles for high drug loading, autonomous gemcitabine/doxorubicin co-delivery, and in-vivo tumor imaging", Journal of Controlled Release, vol. 229,, Mar. 23, 2016, 183-191.
Aymonier, et al., "Hybrids of Silver Nanoparticles with Amphiphilic Hyperbranched Macromolecules Exhibiting Antimicrobial Properties", Chem. Commun., vol. 24, DOI: 10.1039/B208575E, 2002, pp. 3018-3019.
Beumer, et al., "Biocompatibility of a Biodegradable Matrix Used as a Skin Substitute: An in Vivo Evaluation", Journal of Biomedical Materials Research, vol. 28, Available online at https://doi.org/10.1002/jbm.820280504, 1994, pp. 545-552.
Black, et al., "Bacterial Killing by Light-Triggered Release of Silver From Biomimetic Metal Nanorods", Small., vol. 10, No. 1, Jan. 15, 2014, pp. 169-178.
Chan, et al., "Lysozyme-Encapsulated Gold Nanocluster-Based Affinity Mass Spectrometry for Pathogenic Bacteria", Rapid Communications in Mass Spectrometry, vol. 27, Available online at https://doi.org/10.1002/rcm.6674, 2013, pp. 2143-2148.

(Continued)

Primary Examiner — Andrew S Rosenthal
(74) Attorney, Agent, or Firm — Billion & Armitage

(57) ABSTRACT

Embodiments of the present disclosure describe a conjugate comprising a mesoporous nanoparticle having a plurality of pores, wherein the mesoporous nanoparticle is positively charged, wherein an active agent is disposed in the pore; and a plurality of metal nanoclusters, wherein the metal nanocluster has a negative charge, wherein a gate agent is attached to the metal nanocluster. Embodiments of the present disclosure also describe a method of using a conjugate comprising exposing a conjugate to microbes sufficient to release an active agent and treating the microbes with the released active agent. Embodiments of the present disclosure further describe a method of using a conjugate comprising exposing a conjugate to microbes and detecting a presence of the microbes.

18 Claims, 18 Drawing Sheets

(56) References Cited

OTHER PUBLICATIONS

Chang, et al., "Facile Preparation of High-Quantum-Yield Gold Nanoclusters: Application to Probing Mercuric Ions and Biothiols", ACS Applied Materials Interfaces, vol. 6, Available online at https://doi.org/10.1021/am504546f, Oct. 17, 2014, pp. 18824-18831.

Darouiche, "Anti-Infective Efficacy of Silver-Coated Medical Prostheses", Clinical Infectious Diseases, vol. 29, Issue 6, Available online at https://doi.org/10.1086/313561, Dec. 1, 1999, pp. 1371-1377.

Du, et al., "Biomimetic Calcium Phosphate Coatings on Polyactive® 1000/70/30", Journal of Biomedical Materials Research, vol. 59, Available online at https://doi.org/10.1002/jbm.1267, 2002, pp. 535-546.

Ganewatta, et al., "Antibacterial and Biofilm-Disrupting Coatings from Resin Acid-Derived Materials", Biomacromolecules, vol. 16, Available online at https://doi.org/10.1021/acs.biomac.5b01005, Aug. 31, 2015, pp. 3336-3344.

Gunawan, et al., "Induced Adaptation of Bacillus sp. To Antimicrobial Nanosilver", Small, vol. 9, Issue 21,A4vailable online at https://doi.org/10.1002/smll.201300761, Apr. 29, 2013, pp. 3554-3560.

Huang, et al., "In Situ Immobilization of Silver Nanoparticles for Improving Permeability, Antifouling and Anti-Bacterial Properties of Ultrafiltration Membrane", Journal of Membrane Science, vol. 499, Available online at https://doi.org/10.1016/j.memsci.2015.10.055,2016, pp. 269-281.

Jeon, et al., "Preparation and Antibacterial Effects of Ag—SiO2 Thin Films by Sol-Gel Method", Biomaterials, vol. 24, Issue 27, Available online at https://doi.org/10.1016/S0142-9612(03)00415-0, Dec. 2003, pp. 4921-4928.

Kayaci, et al., "Enhanced Thermal Stability of Eugenol by Cyclodextrin Inclusion Complex Encapsulated in Electrospun Polymeric Nanofibers", J. Agric. Food Chem., vol. 61, No. 34, Available online at https://doi.org/10.1021/jf402923c, Jul. 30, 2013, pp. 8156-8165.

Kiristi, et al., "Lysozyme-Based Antibacterial Nanomotors", ACS Nano, vol. 9, No. 9, Available online at https://doi.org/10.1021/acsnano.5b04142, Aug. 26, 2015, pp. 9252-9259.

Li, et al. "Enzyme-Coated Mesoporous Silica Nanoparticles as Efficient Antibacterial Agents in Vivo", Advanced Healthcare Materials, vol. 2, Available online at https://doi.org/10.1002/adhm.201300051, 2013, pp. 1351-1360.

Li, et al. "Rapid Identification of Bacterial Biofilms and Biofilm Wound Models Using a Multichannel Nanosensor", ACS Nano, vol. 8, No. 12, Available online at https://doi.org/10.1021/nn505753s, Dec. 2, 2014, pp. 12014-12019.

Li, et al., "Silver-Resistant Mutants of Escherichia Coli Display Active Efflux of Ag+ and Are Deficient in Porins", J. Bactenol., vol. 179, No. 19, DOI: 10.1128/jb.179.19.6127-6132.1997, Oct. 1997, pp. 6127-6132.

Liu, et al., "One-Pot Synthesis of Gold Nanoclusters With Bright Red Fluorescence and Good Biorecognition Abilities for Visualization Fluorescence Enhancement Detection of E. Coli ", Talanta, vol. 134, Available online at https://doi.org/10.1016/Malanta.2014.10.058,2015, pp. 54-59.

Makarovsky, et al., "Novel Triclosan-Bound Hybrid-Silica Nanoparticles and their Enhanced Antimicrobial Properties", Advanced Functional Materials, vol. 21, Issue 22, Available online at https://doi.org/10.1002/ adfm.201101557, Sep. 13, 2011, pp. 4295-4304.

Kohn, et al., "To Err is Human: Building a Safer Health System", Institute of Medicine, The National Academies Press, 2000, 312 pages.

Meijer, et al., "A Comparative Study of Flexible (Polyactive®) Versus Rigid (Hydroxylapatite) Permucosal Dental Implants. I. Clinical Aspects", Journal of Oral Rehabilitation, vol. 24, Available online at https://doi.org/10.1111/.1365-2842.1997.tb00300.x, 1997, pp. 85-92.

Meng, et al., "Engineered Design of Mesoporous Silica Nanoparticles to Deliver Doxorubicin and P-Glycoprotein siRNA to Overcome Drug Resistance in a Cancer Cell Line", ACS Nano., vol. 4, No. 8, DOI: 10.1021/nn100690m, Aug. 24, 2010, pp. 4539-4550.

Mural, et al., "Polyolefin Based Antibacterial Membranes Derived From PE/PEO Blends Compatibilized With Amine Terminated Graphene Oxide and Maleated PE", Journal of Materials Chemistry A, vol. 2, Sep. 1, 2014, pp. 17635-17648.

Noble, et al., "Digital Drug Delivery: On-Off Ultrasound Controlled Antibiotic Release From Coated Matrices With Negligible Background Leaching", Biomater. Sci., vol. 2, No. 6, Jun. 1, 2014, pp. 839-902.

Oosten, et al., "Real-Time in Vivo Imaging of Invasive- and Biomaterial-Associated Bacterial Infections Using Fluorescently Labelled Vancomycin", Nature Communications, vol. 4, Article No. 2584, Oct. 15, 2013, pp. 1-8.

Park, et al., "Immobilization of Silver Nanoparticle-Decorated Silica Particles on Polyamide Thin Film Composite Membranes for Antibacterial Properties", Journal of Membrane Science, vol. 499, 2016, pp. 80-91.

Pulizzi, "Nanotechnology in Food: Silver-Lined Packaging", Nature Nanotechnology, DOI: 10.1038/nnano.2016.11, Feb. 2016.

Pyo et al., "Ultrabright Luminescence from Gold Nanoclusters: Rigidifying the Au(I)-Thiolate Shell", J. Am. Chem. Soc., vol. 137, Available online at https://doi.org/10.1021/jacs.5b04210, Jun. 10, 2015, pp. 8244-8250.

Radder, et al., "Interface Reactions to PEO/PBT Copolymers (Polyactive) after Implantation in Cortical Bone", Journal of Biomedical Materials Research, vol. 28, DOI: 10.1002/jbm.820280202, 1994, pp. 141-151.

Regiel-Futyra, et al., "Development of Noncytotoxic Chitosan-Gold Nanocomposites as Efficient Antibacterial Materials", ACS Appl. Mater. Interfaces, vol. 7, No. 2, Available online at https://doi.org/10.1021/am508094e, 2015, pp. 1087-1099.

Sambhy, et al., "Silver Bromide Nanoparticle/Polymer Composites: Dual Action Tunable Antimicrobial Materials", J. Am. Chem. Soc., vol. 128, No. 30, Available online at https://doi.org/10.1021/ja061442z, Jul. 7, 2006, pp. 3798-9808.

Schwartz, et al., "Antibacterial Surface Coatings from Zinc Oxide Nanoparticles Embedded in Poly(N-Isopropylacrylamide) Hydrogel Surface Layers", Advanced Functional Materials, vol. 22, Issue 11, Available online at https://doi.org/10.1002/adfm.201102980, Mar. 15, 2012, pp. 2376-2386.

Song, et al., "Engineering the Internal Structure of Magnetic Silica Nanoparticles by Thermal Control", Particle and Particle Systems Characterization, vol. 32, Available online at https://doi.org/10.1002/ppsc.201400118, 2015, pp. 307-312.

Song, et al., "Silica Nanopollens Enhance Adhesion for Long-Term Bacterial Inhibition", J. Am. Chem. Soc., vol. 138, No. 20, Available online at https://doi.org/10.1021/jacs.6b00243, May 3, 2016, pp. 6455-6462.

Taheri, et al., "Substrate Independent Silver Nanoparticle Based Antibacterial Coatings", Biomaterials, vol. 35, Issue 16, Available online at https://doi.org/10.1016/j.biomaterials.2014.02.033, May 2014, pp. 4601-4609.

Wang, et al., "Sustained Antibacterial Activity from Triclosan-Loaded Nanostructured Mesoporous Silicon", Mol. Pharmaceutics, vol. 7, No. 6, Available online at https://doi.org/10.1021/mp100227m, Oct. 25, 2010, pp. 2232-2239.

Wei, et al., "Lysozyme-Stabilized Gold Fluorescent Cluster: Synthesis and Application as Hg2+ Sensor", Analyst, vol. 135, DOI: 10.1039/C0AN00046A, 2010, pp. 1406-1410.

Wong, et al., "Bactericidal and Virucidal Ultrathin Films Assembled Layer by Layer from Polycationic N-Alkylated Polyethylenimines and Polyanions", Biomaterials, vol. 31, Available online at https://doi.org/10.1016/j.biomaterials.2010.01.119, 2010, pp. 4079-4087.

Woranuch, et al., "Eugenol-Loaded Chitosan Nanoparticles: II. Application in Bio-Based Plastics for Active Packaging", Carbohydrate Polymers, vol. 96, No.2, 2013, pp. 586-592.

Wu, et al., "Highly Efficient Antibacterial Surface Grafted with a Triclosan-Decorated Poly(N-Hydroxyethylacrylamide) Brush", ACS Appl. Mater. Interfaces, vol. 7, No. 12, Available online at https://doi.org/10.1021/acsami.5b01210, Mar. 10, 2015, pp. 7008-7015.

(56) References Cited

OTHER PUBLICATIONS

Xie, et al., "Silver Nanoparticles and Growth Factors Incorporated Hydroxyapatite Coatings on Metallic Implant Surfaces for Enhancement of Osteoinductivity and Antibacterial Properties", ACS Appl. Mater. Interfaces, vol. 6, Available online at https://doi.org/10.1021/am501428e, Apr. 10, 2014, pp. 8580-8589.

* cited by examiner

AuNC@Lys

MSN-AuNC@Lys

Kanamycin-loaded
MSN-AuNC@Lys

RhodamineB-loaded
MSN-AuNC@Lys

NANOCLUSTER CAPPED MESOPOROUS NANOPARTICLES, METHODS OF MAKING AND USE

BACKGROUND

The ability of microbes to survive, grow and colonize on hospital surfaces and patient care devices is considered as a key challenge in controlling the spread of healthcare-associated infections (HAIs). In the past 20 years these infections have increased by 36%, escalating the urgency for developing antibacterial surfaces to prevent bacterial growth and, hence, biofilm formation. Nanosilver is one of the most used antimicrobial ingredients in clinical technologies. Hybrids of silver nanoparticles (AgNPs) and amphiphilic hyperbranched macromolecules constitute effective antibacterial surface coating agents. However, the extensive exposure of bacteria to AgNPs and Ag containing membranes endowed the development of Ag resistant microorganisms. Furthermore, recent reports on AgNPs leaching from packaging and storage products constitutes a major health concern. Other biocidal agents were incorporated in coating matrices to enhance their antibacterial properties, such as Zinc oxide, triclosan, eugenol, and antibiotics with leaching still being the major drawback. Moreover, these studies are mainly focused on optimizing the antibacterial activity of coating matrices rather than bacterial detection, where the latter is important to control and verify surface contamination. The unique physicochemical properties of NPs significantly enhanced bacterial sensing strategies. Functionalized AuNPs have been shown to aid in the detection of bacteria and biofilm formation. Lysozyme functionalized gold hybrids were used to detect bacteria through the multivalent interactions between lysozyme and N-acetylglucosamine on the peptidoglycans on bacterial cell walls. However, developing a biocompatible coating that can simultaneously detect (by the naked eye under UV light) and inhibit bacterial growth with zero nano-component leaching risk has so far proved to be very challenging.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

SUMMARY

In general, embodiments of the present disclosure describe conjugates and methods of using a conjugate.

Accordingly, embodiments of the present disclosure describe a mesoporous nanoparticle having a plurality of pores, wherein the mesoporous nanoparticle is positively charged, wherein an active agent is disposed in the pore; a plurality of metal nanoclusters, wherein the metal nanocluster has a negative charge, wherein a gate agent is attached to the metal nanocluster. In many embodiments, an electrostatic interaction causes the metal nanoclusters to seal in the active agent in the pore, the gate agent is positioned on the outside surface of the conjugate so that it interacts with a gate target, and/or the active agent moves out of the pore upon removal of the metal nanocluster.

Embodiments of the present disclosure further describe a method of using a conjugate comprising exposing a conjugate to microbes sufficient to release an active agent and treating the microbes with the released active agent. In many embodiments, the conjugate comprises an active agent disposed in a plurality of pores of a mesoporous nanoparticle; a plurality of metal nanoclusters sealing in the active agent via an electrostatic interaction; and a gate agent attached to the metal nanoclusters and positioned on an outside of the conjugate. The gate agent may interact with a gate target sufficient to remove the metal nanocluster from the mesoporous nanoparticle and release the active agent.

Another embodiment of the present disclosure is a method of using a conjugate comprising exposing a conjugate to microbes and detecting a presence of the microbes. In many embodiments, the conjugate comprises an active agent disposed in a plurality of pores of a mesoporous nanoparticle; a plurality of metal nanoclusters sealing in the active agent via an electrostatic interaction; and a gate agent attached to the metal nanoclusters and positioned on an outside of the conjugate.

The details of one or more examples are set forth in the description below. Other features, objects, and advantages will be apparent from the description and from the claims.

BRIEF DESCRIPTION OF THE DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION

Figure 1:
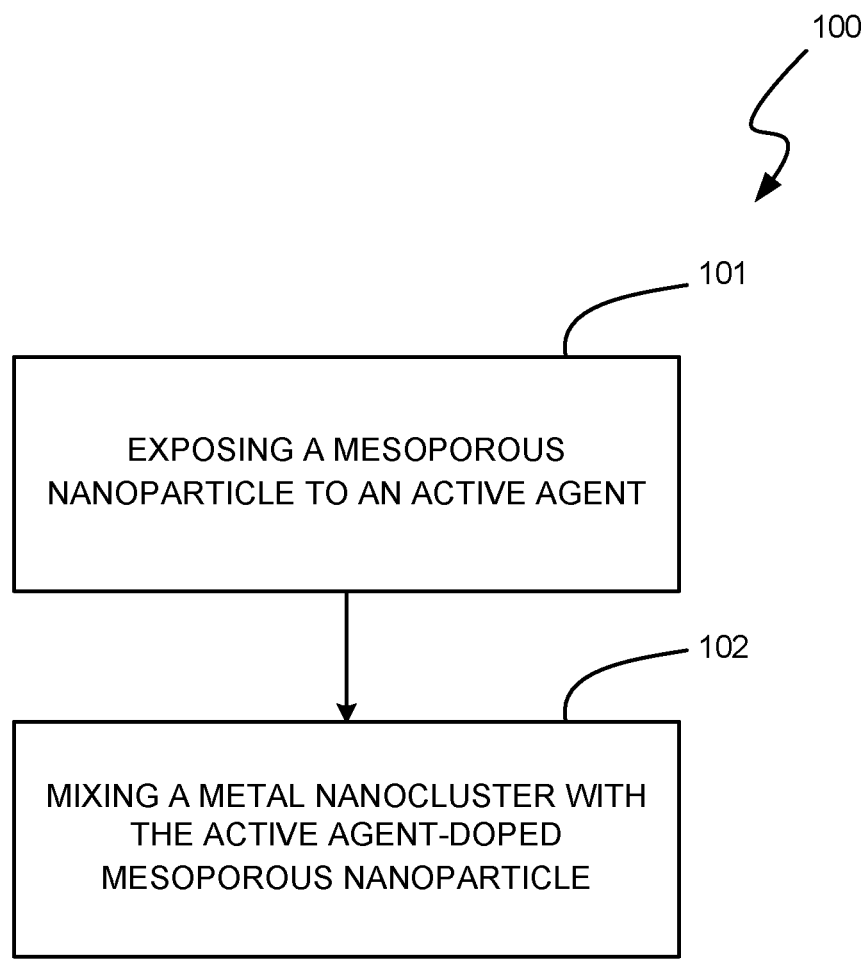
FIG. 1 is a flowchart of a method of making a conjugate, according to one or more embodiments of the present disclosure.

The invention of the present disclosure generally relates to novel conjugates and various applications of the conjugates. The conjugates of the present disclosure may include mesoporous nanoparticles containing active agents disposed within pores of the mesoporous nanoparticles. The active agent-containing pores of the mesoporous nanoparticle may be capped by metal nanoclusters, wherein the metal nanoclusters include gate agents, which are positioned on an outside of the conjugate. The conjugates provide novel functionality. For example, upon exposure to a gate target, the metal nanocluster may detach from the mesoporous nanoparticle in response to an interaction between the gate agent and the gate target. The metal nanocluster's detachment from the mesoporous nanoparticle releases the active agent. As the activity of the gate agent increases, the fluorescence of the metal nanocluster may progressively decrease. In this way, the conjugates of the present disclosure may provide dual functionality with respect to sensing and controlled release. For example, the conjugates may be included in a biocompatible coating that can simultaneously detect a presence of bacteria and kill the bacteria or inhibit bacterial growth, with zero nano-component leaching risk. Moreover, the conjugates may be scaled up with high uniformity and reproducibililty. Other embodiments described herein relate to methods of making conjugates, methods of using conjugates, and various other applications of conjugates.

Definitions

As used herein, the term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

As used herein, the term "microbe" includes any single-celled or multicellular organism (e.g., microscopic organism). Microbe, for example, may include, among other things, one or more of bacteria, protozoan, algae, and fungi.

As used herein, the terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium*, or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

As used herein, the term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia.*

As used herein, the term "algae" as used herein includes, without limitations microalgae and filamentous algae such as *Anacystis nidulans, Scenedesmus* sp., *Chlamydomonas* sp., *Clorella* sp., *Dunaliella* sp., *Euglena* so., *Prymnesium* sp., *Porphyridium* sp., *Synechoccus* sp., *Botryococcus braunii, Crypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp., *Senedesmus obliquus,* and *Tetraselmis sueica* as well as algae belonging to any of *Spirogyra, Cladophora, Vaucheria, Pithophora* and *Enteromorpha* genera.

As used herein, the term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

Embodiments of the present disclosure include conjugates, methods of making conjugates, methods of using conjugates, and the like. In an embodiment, the conjugates can be made biocompatible, non-toxic, and are easy to make, as well as embodiments can be made multifunctional, all of which give conjugates of the present disclosure one or more advantages as compared to others systems.

In an embodiment, the conjugate includes a mesoporous nanoparticle having a plurality of pores having a charge or net charge (e.g., positively charged). The conjugate includes one or more active agents (e.g., the same or different types of active agents) (e.g., an antimicrobial) disposed within some (e.g., about 70-100%, about 80-100%, about 90-100%, about 95-100% or about 99-100% of the pores) or all of the pores. The conjugate includes a plurality of metal nanoclusters that have the opposite charge of the mesoporous nanoparticle (e.g., negatively charged) while each also have a gate agent (e.g., the same or different types of gate agents) (e.g., a lysozyme) (e.g., reduced metal salt) (e.g., lysozyme stabilized gold nanocluster). The electrostatic interaction (due to the fact they have opposite charges) of the mesoporous nanoparticle and the metal nanocluster cause the metal nanoclusters to seal in the active agent in the pores of the mesoporous nanoparticle. The gate agent is positioned on the outside of the conjugate so that when the gate agent interacts with the gate target (e.g., cell wall) the metal nanocluster dissociates from the mesoporous nanoparticle and the active agent moves out of the pore. In this regard, the conjugate, in an embodiment, can be used to sense and inhibit microbial contamination via a controlled release mechanism that is only triggered by microbes. In addition, variation and eventually disappearance of the red fluorescence of the conjugate under UV light signals microbial infection.

The high porosity of the mesoporous nanostructure provides for the ability to include several functionalities as well as the ability to provide a high amount of functional cargo (active agent). In addition, the conjugate can combine different loading strategies (e.g., one of or both of the active agent and the gate agent, where each can be included as different types) in the same conjugate to address different issues (e.g., address both microbial and corrosion activity of a substrate).

In an embodiment, the mesoporous nanoparticle includes a plurality of pores having dimensions so that the active agent can become disposed therein. The pores can have any shape. For example, the pores may be cylindrical and/or spherical in shape. The mesoporous nanoparticle has a charge or net charge that is the opposite that of the metal nanocluster. In an embodiment, the mesoporous nanoparticles has a positive charge while the metal nanocluster has a negative charge.

The mesoporous nanoparticle can have pores. The pore size (e.g., pore diameter or average pore diameter) can be sufficiently large to permit loading of cargo molecules (e.g., active agents) and sufficiently small to permit capping by the metal nanocluster-gate agent complexes. In an embodiment, the mesoporous nanoparticle can have pores having a pore opening of a diameter (or longest dimension) of about 2 to 4 nm. In an embodiment, the pores can extend into the mesoporous nanoparticle to a depth of about 10 to 100 nm. In an embodiment, the mesoporous nanoparticle can have a spherical or semispherical shape. The mesoporous nanoparticle can have a porosity of about 600 to 1300 m2/g. In an embodiment, the mesoporous nanoparticle can have a diameter (or lonest dimension) of about 100 to 400 nm or about 300 nm. In an embodiment, the mesoporous nanoparticle can include a mesoporous silica nanoparticle, a mesoporous silicon nanoparticle, mesoporous titania, mesoporous carbon, metal-organic framework, and/or zeolite.

In an embodiment, the active agent can be a chemical or biological component that has a purpose to act upon an active agent target upon release from the conjugate. For example, the active material can include an antimicrobial agent (e.g., antibacterial agent, antifungal agent, antiviral agent, and the like), anti-corrosion agent, antioxidant agent, antiscalant agent, anticoagulant, and surfactant. In a particular embodiment, the active agent can be an antibacterial agent (e.g., kanamycin), so upon release from the mesoporous nanoparticle the antibacterial agent can act upon the active agent target, bacteria (e.g., a bacterial infection). In an embodiment, the mesoporous nanoparticle can include about 30 to 60% of the active agent.

In an embodiment, the antibacterial agent can include kanamycin, eugenol, triclosan, piperine, or a combination thereof. In an embodiment, the antifungal agent can include bifonazole, clotrimazole, fluconazole, or a combination thereof. In an embodiment, the antiviral agent can include abcavir, balvir, fosfonet, or a combination thereof.

In an embodiment, the anti-corrosion agent can include benzotriazole, zinc phosphate, antiseptics, caffeine, or a combination thereof.

In an embodiment, the antioxidant agent can include glutathione, carotenes, or a combination thereof.

In an embodiment the metal nanocluster (or in an alternative embodiment, a nanoparticle) can include metal nanoclusters having a charge opposite that of the mesoporous nanoparticle. For example, the metal nanocluster has a negative or net negative charge when the mesoporous nanoparticles has a positive charge. For example, the metal nanocluster is sized so that it prevents or substantially (e.g., 90% or more, or 95% or more) prevents the active agent from escaping the pore of the mesoporous nanostructure. In an embodiment, the metal nanocluster has spherical or semi-spherical shape. In an embodiment, the longest dimension (e.g., a diameter) has a length of about 10 to 1000 nm, about 100 to 800 nm, or about 100 to 500 nm. In an embodiment, the metal nanocluster can be a transition metal nanocluster or precious metal nanocluster such as gold nanocluster, silver nanocluster or copper nanocluster. In many embodiments, the metal nanocluster may be fluorescent to provide, among other things, detection functionality. For example, as the activity of the gate agent increases, the fluorescence of the metal nanocluster may decrease, signaling bacteria detection.

In addition, the metal nanocluster has one or more gate agents attached to the metal nanocluster. The gate agent acts on a gate target. For example, the gate agent may act upon the gate target to cause a response in the gate target that then allows the active agent to act upon the active agent target. In an embodiment the gate target is the cell wall of bacteria and the active agent target is the bacteria. So after the gate agent attacks and disrupts the bacteria cell wall, the active agent (e.g., an antibacterial agent) can attack the bacteria and kill it or inhibit its growth. In some embodiments the gate target and the active agent target may be the same thing or part(s) of the same thing. In other embodiments, the gate target and the active agent target may be distinct but related as gate agent may need to act upon the gate target prior to the active agent being able to act upon the active agent target. As can be understood from the foregoing, the selection of the active agent and the gate agent are coordinated so that each can act upon gate target and the active agent target, respectively, and cause the desired outcome. In many embodiments, the gate agent includes lysozyme. In other embodiments, the gate agent includes Bovine Serum Albumin (BSA).

Embodiments of the present disclosure include methods of making a conjugate, according to one or more embodiments of the present disclosure. For example, FIG. 1 is a flowchart of a method 100 of making a conjugate, according to one or more embodiments of the present disclosure. As shown in FIG. 1, the method 100 of making the conjugate can include exposing 101 the mesoporous nanoparticle to the active agent under conditions so that the active agent becomes disposed in the pores of the mesoporous nanoparticle. Subsequently, the metal nanocluster having the opposite charge of the mesoporous nanoparticle is mixed 102 with the active agent doped mesoporous nanoparticles, and the electrostatic interaction causes the metal nanoclusters to become disposed onto the surface of the mesoporous nanoparticle substantially blocking (e.g., blocking) the pore entrance so that the active agent is trapped within the pores until the metal nanoclusters are caused to be released from the mesoporous nanoparticle.

Exposing may include one or more of dispersing, adding, providing, mixing, contacting, sonicating, and any method of bringing two components into physical and/or chemical proximity. In many embodiments, exposing includes dispersing the mesoporous nanoparticle in a solution (e.g., buffer saline solution, such as phosphate buffer saline, and the like) mixed with the active agent. The exposing may, among other things, form the active agent-doped mesoporous nanoparticle. Mixing may similarly include one or more of exposing, dispersing, adding, providing, contacting, sonicating, and any method of bringing two components into physical and/or chemical proximity sufficient to cause the metal nanoclusters to become disposed via electrostatic interaction onto the surface of the mesoporous nanoparticle. Additional details regarding the method of making the conjugate are provided in the Example.

Embodiments of the present disclosure may include a coating comprising a polymer and a conjugate. The conjugate may include any of the conjugates described herein and/or the polymer may include any of the polymers described herein. Embodiments of the present disclosure may include a coating disposed on the surface of the structure, wherein the coating includes a polymer and a conjugate. The conjugate may similarly include any of the conjugates described herein and/or the polymer may include any of the polymers described herein.

In an embodiment, the conjugate can be included in a coating or film and/or disposed onto a structure. The coating or film can include a polymer and the conjugate. In an embodiment the conjugate can still interact with the environment adjacent the coating or film. In an embodiment, the conjugate can be dispersed homogenously within coating or film with no phase separation, precipitation of the polymer, and/or zero nanoparticle leaching.

The leaching experiments were performed on the mixed matrix coating in three media: in water (with pH of 7 and 5) and in saline solution. The leaching of gold from the coating was studied for 10 days. The resulting solutions were analyzed every 24 h for 10 days with an Inductively Coupled Plasma Mass Spectrometry ICP-MS (Elan DRC II, PerkinElmer) to quantify the concentration of gold. The membranes were then digested and the results were presented in term of percentage of released gold by the total amount in the membrane. The results showed that there is no release of gold in the three medias and the difference is the margin of error of the machine.

The coating or film can include about 5 to 40% of the conjugate. In an embodiment, the coating or film can have a thickness of about 10 to 100 µm. In an embodiment, the polymer can be an amphiphilic polymer and/or miscible with water. For example, the polymer can be polymer can be one of the following: poly(ethylene oxide)/poly(butylene terephthalate), pebax, polyamide, polyetherimide, polydimethylsiloxane, and a combination thereof.

In an exemplary embodiment, where the active agent is antimicrobial agent, the coatings or films including the conjugate can have an antimicrobial characteristic (e.g., kills about 70% or more, about 80% or more, about 90% or more, about 95% or more, or about 99% or more (where the upper limit is 100%) of the microorganisms (e.g., bacteria) on the surface and/or reduces the amount of microorganisms that form or grow on the surface by about 70% or more, about 80% or more, about 90% or more, about 95% or more, or about 99% or more (where the upper limit is 100%), as compared to a similar surface without the conjugate or coatings or films including the conjugate disposed on the surface. For example, embodiments of the present disclosure can be used to prevent biofilm growth and/or remove a biofilm.

In an embodiment, the structure comprising the conjugate-containing coating or film may exhibit a substantially uniform (e.g., uniform) coating/film deposed on the structure. In addition or in the alternative, the structure comprising the conjugate-containing coating or film may exhibit an increased surface roughness. In some embodiments, the surface roughness or increased surface roughness may aid conjugates to attach strongly to bacteria so they efficiently destroy the cell wall, for example, by the action of the gate agent.

In an embodiment, the structures can include those that may be exposed to microorganisms and/or that microorganisms can grow on such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. The structures may also include live biologic structures (or surfaces of live biologic structures) such as seeds for agricultural uses, tree limbs, trunk, and teeth (in a human or animal). In particular embodiments, the structure can include re-usable dental plates, textile articles, filters packaging materials (e.g., food, meat, poultry, and the like food packaging materials), plastic structures, glass metals, metal alloys, metal, tile, stone, ceramic, marble, granite, and a combination thereof.

Figure 2:
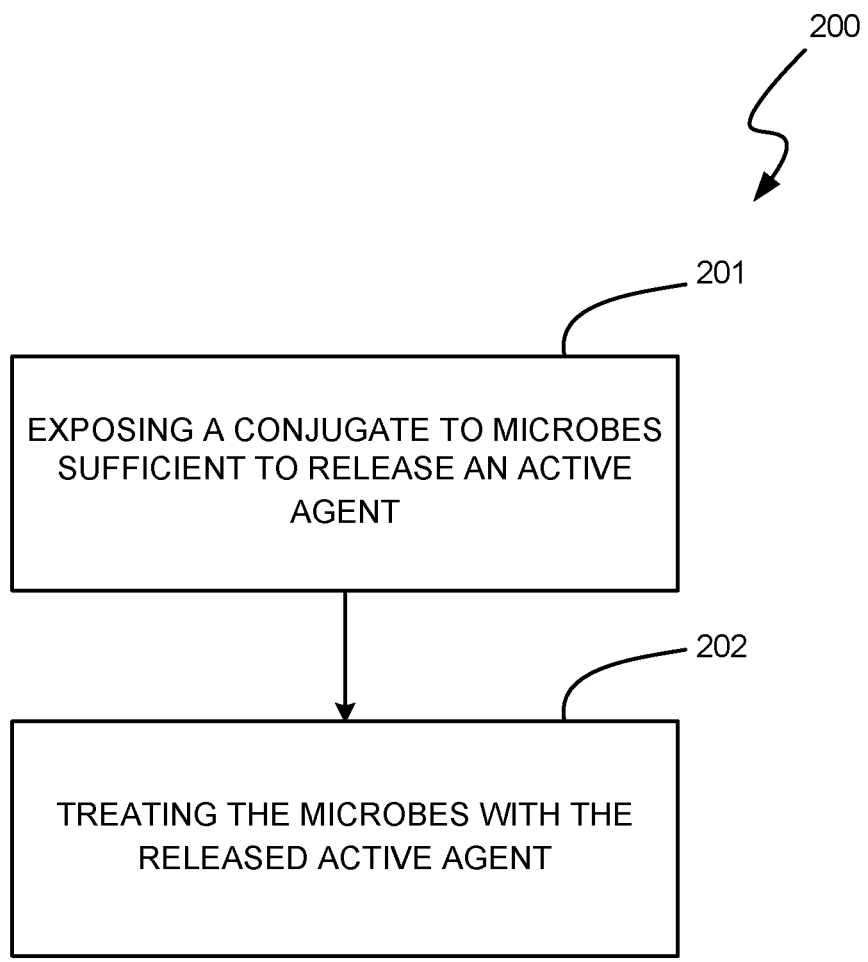
FIG. 2 is a flowchart of a method of using a conjugate to treat microbes, according to one or more embodiments of the present disclosure.

Embodiments of the present disclosure also describe methods of using a conjugate. A flowchart of a method of using a conjugate is shown in FIG. 2, according to one or more embodiments in the present disclosure. As shown in FIG. 2, the method comprises exposing 201 a conjugate to microbes sufficient to release an active agent, wherein the conjugate comprises the active agent disposed in pores of a mesoporous nanoparticle; a plurality of metal nanoclusters sealing in the active agent; and a gate agent attached to the metal nanoclusters and positioned on an outside of the conjugate. The gate agent may interact with a gate target sufficient to remove the metal nanocluster from the mesoporous nanoparticle and release the active agent. The method also comprises one or more of treating 202 microbial growth, preventing microbial growth (not shown), and killing (not shown) microbes with the released active agent. In addition, the method may include any of the embodiments disclosed herein (e.g., conjugates, coatings, films, substrates, etc.).

Exposing may include bringing into proximity sufficient to initiate any action. For example, exposing may include bringing the conjugate into proximity with the microbes sufficient to release the active agent. The active agent may be released by the activity of the gate agent. For example, the gate agent may interact (e.g., engage, approach, contact, etc. to attack, destroy, degrade) with a cell wall of the microbe sufficient to detach the metal nanocluster from the microporous nanoparticle and release the active agent from the pores. The exposing may occur in a medium of any phase (e.g., gas/vapor, liquid, solid).

Treating or preventing microbial growth (e.g., biofilm growth), specifically bacterial growth (e.g., antimicrobial characteristic), may include inhibiting microbial growth and/or killing microbes. In an embodiment, treating or preventing includes inhibiting and/or killing about 70% or more, about 80% or more, about 90% or more, about 95% or more, or about 99% or more (where the upper limit is 100%) of the microorganisms (e.g., bacteria) on the surface and/or reduces the amount of microorganisms that form or grow on the surface by about 70% or more, about 80% or more, about 90% or more, about 95% or more, or about 99% or more (where the upper limit is 100%), as compared to a similar surface without the conjugate or coatings or films including the conjugate disposed on the surface.

In some embodiments (not shown), the method may further comprising detecting a presence of a microbe. Detecting may include one or more of measuring a fluorescence signal and observing a decrease in fluorescence. Known techniques and/or instruments may be used to measure a fluorescence signal and/or observe a decrease in fluorescence. In many embodiments, the fluorescence of the conjugate decreases upon exposing the conjugate to microbes. The decrease in fluorescence may be detected under UV light without the aid of any instruments (e.g., detected by the naked eye).

Figure 3:
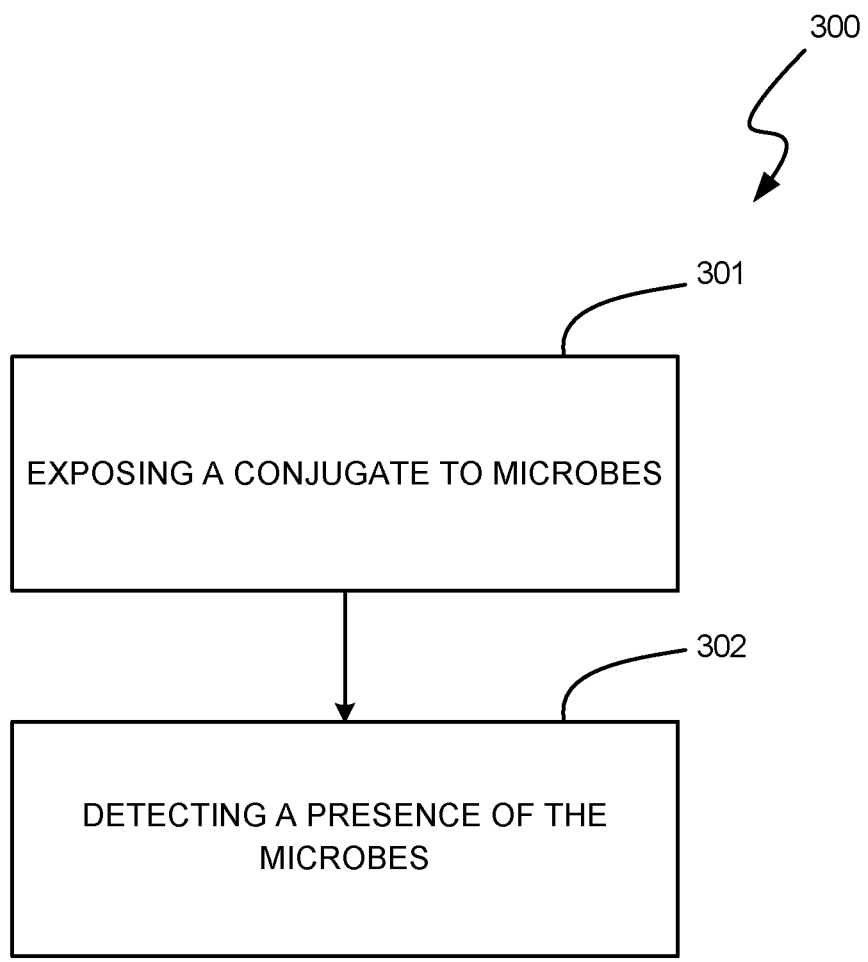
FIG. 3 is a flowchart of a method of using a conjugate to detect a presence of microbes, according to one or more embodiments of the present disclosure.

Another method of using a conjugate is shown in FIG. 3, according to one or more embodiments of the present disclosure. As shown in FIG. 3, the method 300 comprises exposing 301 a conjugate to microbes, the conjugate comprising: the active agent disposed in pores of a mesoporous nanoparticle; a plurality of metal nanoclusters sealing in the active agent; and a gate agent attached to the metal nanoclusters and positioned on an outside of the conjugate. The method further comprises detecting 302 a presence of the microbes. In some embodiments (not shown), the method may further comprise one or more of treating microbial growth, preventing microbial growth, and killing microbes with the released active agent. The embodiments and discussion of the present disclosure are hereby incorporated by reference in its entirety.

An embodiment of the present disclosure includes a method of providing a substrate having a conjugate that is disposed on a surface of the substrate. The active agent can be an antimicrobial agent such as an antibacterial agent. The substrate is exposed to a microbe (e.g., bacteria). The exposure of the substrate can occur in numerous different ways depending upon the substrate. As discussed above, the conjugate includes the gate agent (e.g., lysozyme) on the metal nanoclusters that can interact with the gate target (e.g., cell wall of the bacteria). The interaction of the lysozyme with the cell wall causes the metal nanoclusters to dissociate with the mesoporous nanoparticle and the antibacterial agent is released from the conjugate and can act upon the bacterial. Interaction of the antibacterial agent can kill the bacteria and/or inhibit/prevent the growth the bacteria.

Figure 4:
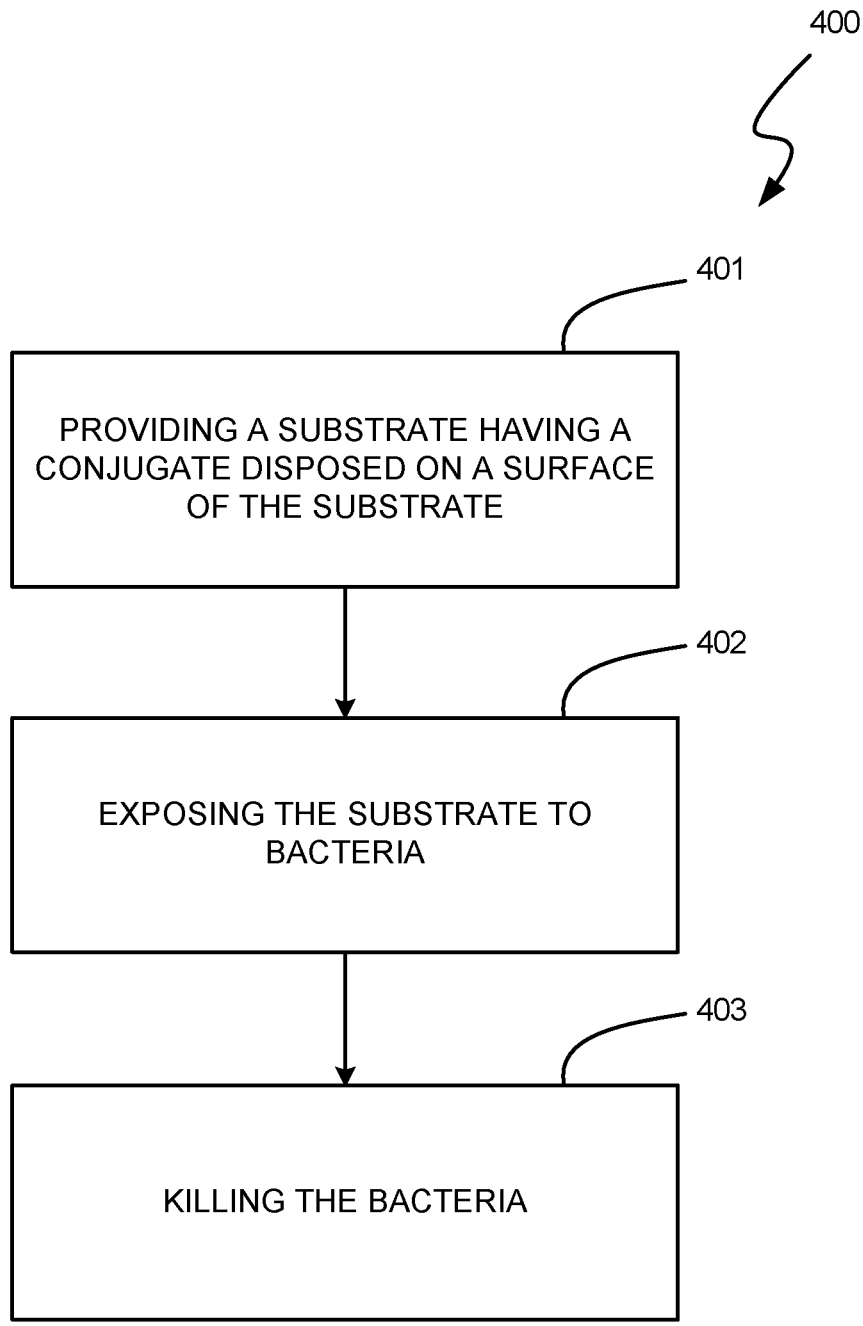
FIG. 4 is a flowchart of a method of treating or preventing microbial growth, according to one or more embodiments of the present disclosure.

For example, FIG. 4 is a flowchart of a method 400 of treating or preventing microbial growth, according to one or more embodiments of the present disclosure. The method may include providing 401 a substrate having a conjugate that is disposed on a surface of the substrate, wherein the active agent is an antibacterial agent; exposing 402 the substrate to bacteria, wherein the gate agent on the metal nanoclusters interact with the cell wall of the bacteria, wherein the metal nanoclusters are removed from the conjugate and the antibacterial agent is released from the conjugate; and killing 403 the bacteria with the released antibacterial agent. In an embodiment, the conjugate may be part of a coating that is disposed on the surface of the substrate.

In addition or in the alternative to the above, in an embodiment, exposing 402 may include bringing into proximity sufficient to initiate any interaction. For example, exposing may include bringing the conjugate-containing substrate into proximity with bacteria sufficient for the gate agent to interact (e.g., engage, approach, contact, etc. to attack, destroy, degrade) with the cell wall of the bacteria. The exposing may occur in a medium of any phase (e.g., gas/vapor, liquid, solid).

In an embodiment, treating or preventing includes killing 403 about 70% or more, about 80% or more, about 90% or more, about 95% or more, or about 99% or more (where the upper limit is 100%) of the microorganisms (e.g., bacteria) on the surface and/or reduces the amount of microorganisms that form or grow on the surface by about 70% or more, about 80% or more, about 90% or more, about 95% or more, or about 99% or more (where the upper limit is 100%), as compared to a similar surface without the conjugate or coatings or films including the conjugate disposed on the surface.

An embodiment of the present disclosure includes methods of detecting the presence and/or exposure of the substrate to bacteria by monitoring the fluorescence of the conjugate over time. In an embodiment, the method can include providing a substrate having a conjugate that is disposed on a surface of the substrate. The active agent can be an antibacterial agent. The fluorescent signal of the conjugate can be measured as a function of time. The fluorescent signal of the conjugate decreases upon exposure the substrate to bacteria as compared to when bacteria is not present. The gate agent (e.g., lysozymes) on the metal nanoclusters interact with the cell wall of the bacteria and the metal nanoclusters are removed from the conjugate. Since the fluorescent signal is derived from the presence of the metal nanoclusters, as the metal nanoclusters dissociate from the conjugate, the fluorescent signal decreases. As a result, the fluorescent signal can be used to detect the presence and/or exposure of the substrate to bacteria. And as stated above, the bacteria will be killed by the release of the active agent, the antibacterial agent.

Figure 5:
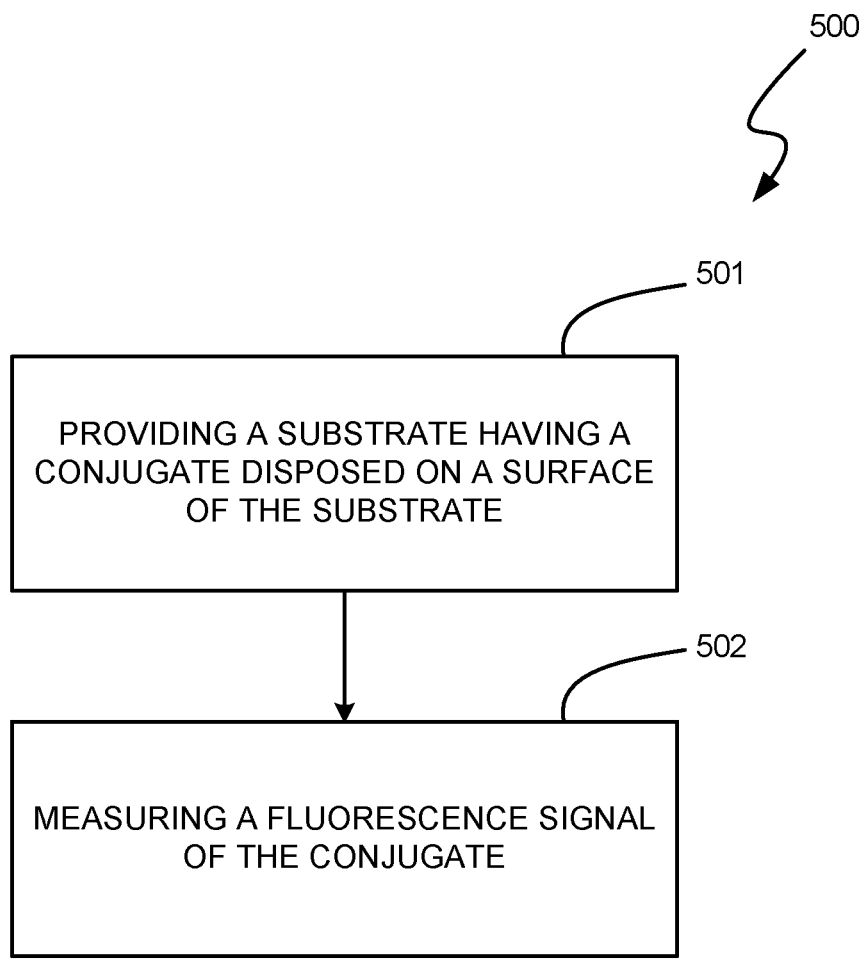
FIG. 5 is a flowchart of a method of detecting a presence of bacteria, according to one or more embodiments of the present disclosure.

For example, FIG. 5 is a flowchart of a method 300 of detecting the presence of bacteria, according to one or more embodiments of the present disclosure. As shown in FIG. 5, the method may include providing 501 a substrate having a conjugate of claim 1 that is disposed on a surface of the substrate, wherein the active agent is an antibacterial agent; and measuring 502 a fluorescence signal of the conjugate, wherein the fluorescence of the conjugate decreases upon exposure the substrate to bacteria as compared to when bacteria is not present, wherein the gate agent on the metal nanoclusters interact with the cell wall of the bacteria and the metal nanoclusters are removed from the conjugate.

In an embodiment, a mesoporous silicon nanoparticle can be used as the mesoporous nanoparticle, kanamycin can be the active agent, a lysozyme stabilized gold cluster can be used as the gate agent, to produce a conjugate (MSN-AuNCs@lys NPs) for the delivery of kanamycin. In an embodiment, MSN-AuNCs@lys NPs were successfully doped in polyactive polymer and used to coat a material. The MSN-AuNCs@lys NPs showed zero-premature leakage and responded quickly to the bacteria presence by releasing the antimicrobial agent. The MSN-AuNCs@lys NPs showed a great capability for the bacterial detection. The absence of surface fluorescence indicates bacterial contamination, while fluorinated surfaces are enough indicators of surface free bacteria. In particular, the absence of surface fluorescence showing blue color under UV light flags bacterial contamination, while red fluorescent surfaces signals bacteria-free environment.

In an embodiment, X-ray dental imaging plates (PSP plate), which are reusable, were coated with MSN-AuNCs@lys NPs. These plates are inserted into a plastic sleeve, or "barrier envelope," prior to insertion into the patient's mouth. The possibility of transferring contaminated material to patient's mouth, if integrity of plate's protective envelope is jeopardized, is very high. Thus, inclusion of MSN-AuNCs@lys NPs on the PSP plate can be advantageous. Use of the MSN-AuNCs@lys NPs in a coating on a PSP plate showed reproducible sensitivity as well as inhibition of bacterial growth. The quality of the images obtained with the coated plate were identical to the uncoated ones proving the promising real-life applicability of this system. Based on these results, MSN-AuNCs@lys NPs can be used in the monitoring and inhibition of bacterial contamination on hospital surfaces, medical equipment, and other radiographic patient care devices. Additional details are provided in the Example.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

EXAMPLE

Figure 6:
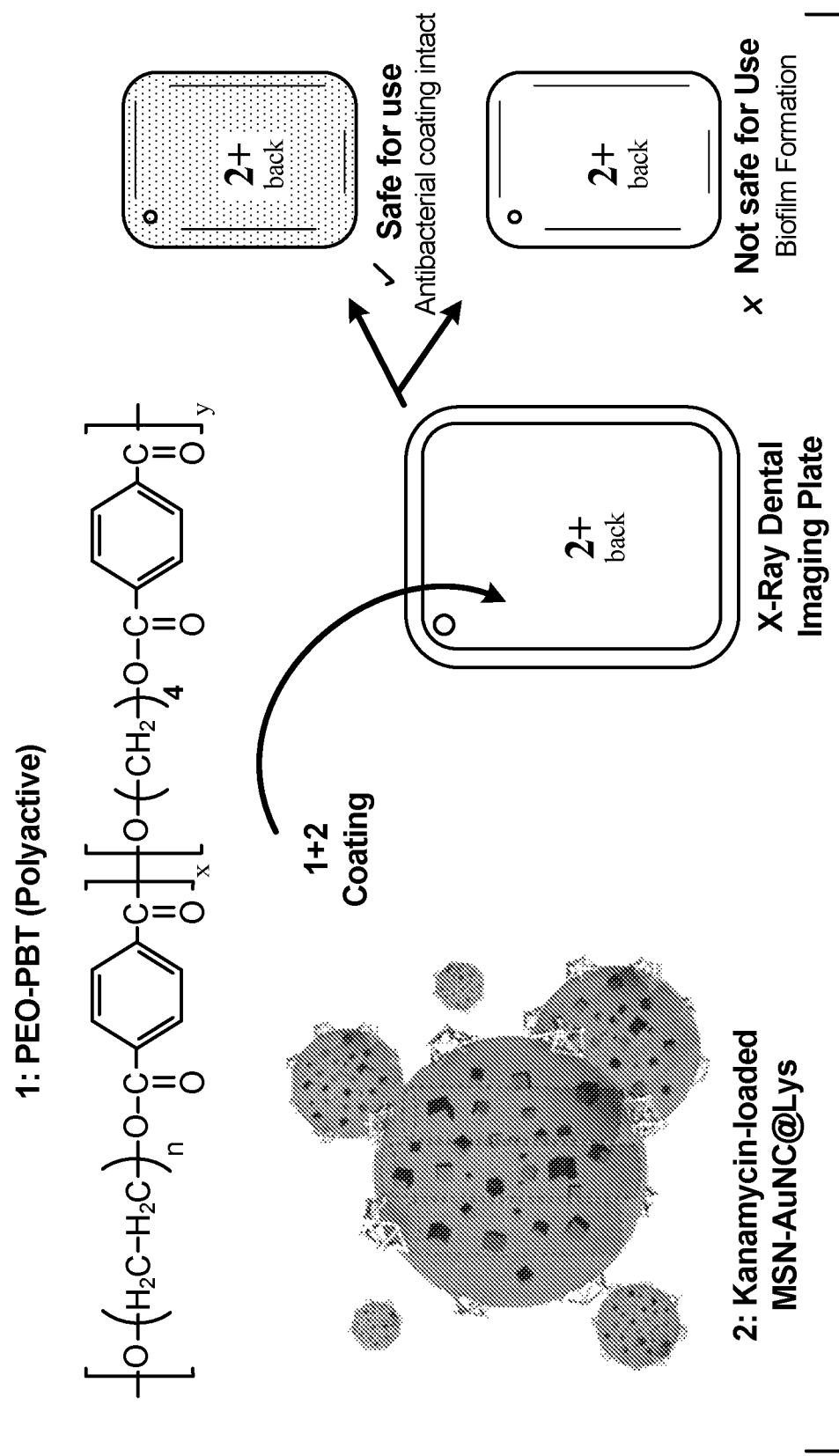
FIG. 6 is a schematic diagram depicting an antibacterial membrane nanocomposite based on polyactive and MSN-AuNC@Lys NPs, according to one or more embodiments of the present disclosure.

In this example, the synthesis of lysozyme templated colloidal gold nanoclusters (AuNCs@lys) capped kanamycin loaded mesoporous silica nanoparticles (kanamycin-MSNs) as polymer matrix nano-fillers is disclosed. Electrostatic self-assembly of negatively charged and fluorescent AuNCs on positively charged MSNs provided tightly gated antibacterial smart carriers. Only upon encountering bacteria, AuNCs@lys detach from MSN surface (due to the interaction of lysozyme with bacterial cell wall), which releases the entrapped antibacterial cargo. Concurrently, loss of AuNCs@lys red fluorescence can be efficiently detected affording an in-situ bacterial sensing platform. MSN-AuNCs@lys NPs were uniformly dispersed in poly(ethylene oxide)/poly(butylene terephthalate) (PEO-PBT) polymer matrix with strong interfacial interaction and no NPs leaching (FIG. 6). This mixed-matrix coating is biocompatible and was successfully scaled up with high uniformity and reproducibility. To highlight a real life application, this system was spin-coated on dental imaging plates as these reusable dental care products are at high risk of oral bacteria contamination. This smart coating successfully detected and inhibited bacterial infection while maintaining the quality of the dental images obtained with these plates.

Apart from anti-microbial activity, the protein can be properly chosen to give more functionality to the system. The lysozyme can be replaced by Bovine Serum Albumin BSA, for example, to make a pH-sensitive nanocarrier for anti-corrosion coating. Several other types of protein can be properly used based on the trigger and the functionality of the nanocarrier. The properly factionalized MSN can be incorporated to any kind of coating, textile, and membrane used for water recovery processes.

Experimental Section

Synthesis of MSN. CTAB (0.80 g) was stirred in deionized water (384 mL). A concentrated aqueous solution of NaOH (2.8 mL, 2 M) was added, and the temperature of the solution was set to 80° C. After 30 min, TEOS (4 mL) was added dropwise while stirring and the sol-gel process was conducted for 2 h. Finally, the solid product was filtered, washed with deionized water and methanol, and dried in air. The white powder was refluxed for 16 h in a mixture of methanol (80 mL) and concentrated HCl (1 mL, 37%), and filtered and washed extensively with water and ethanol. Two other-extractions were carried via ammonium nitrate ethanol solutions (6 g·L$^{-1}$), followed by ethanol washings to ensure the complete CTAB removal. The resulting surfactant-free MSN was dried under vacuum for few hours.

Synthesis of MSN-NH2. MSN-CTAB (200 mg) was suspended in anhydrous toluene (30 mL), APTES (100 mL) was added to the mixture, and the solution was refluxed for 24 h. Then, the solution was cooled down to room temperature, centrifuged at 1400 rpm for 5 min, washed several times with EtOH, and dried at room temperature overnight. The resulting amino functionalized NPs were surfactant extracted in the same manner described for MSN-CTAB.

Synthesis of AuNC@Lys. AuNC@Lys were synthesized according to a previously reported procedure. Briefly, an aqueous solution of $HAuCl_4$ solution (5 mL, 10 mM) was added to a lysozyme solution (5 mL, 50 mg·$mL^{-1}$) under vigorous stirring at 37° C. After 10 min, an aqueous solution of NaOH (500 mL, 1 M) was introduced, and the mixture was incubated at 37° C. for 12 h. The final solution was stored at 4° C.

Synthesis of MSN-AuNC@ lys. $MSN-NH_2$ (20 mg) were dispersed in phosphate buffer saline (20 mL, 10 mM, pH 7.4), and the solution was sonicated for 1 min. The as-prepared AuNC@lys solution (5 mL) was then added into the NPs solution, and the mixture was stirred at room temperature for 12 h. Finally, the resulting MSN-AuNC@lys NPs were collected by centrifugation (4000 rpm, 10 min), and washed with PBS solution several times.

Preparation of RhB and kanamycin Loaded MSN-AuNC@lys. $MSN-NH_2$ (200 mg) were dispersed in PBS (25 mL), mixed with RhB/kanamycin (5 mg), and stirred at room temperature for 24 h. The RhB-loaded NPs were then collected via centrifugation (4000 rpm, 10 min), washed once, and dried under vacuum for few hours. The AuNC@lys PBS solution was mixed with loaded MSN-$NH_2$, and stirred for 6 h, followed by centrifugation and repeated washings with PBS.

Bacterial viability determination. E. coli was cultured in LB medium at 37° C. on a shaker at 240 rpm for 4 h. Then, the bacterial suspension was washed twice by centrifugation (4000 rpm, 5 minutes) and re-suspended in LB media. The optical density at 600 nm ($OD_{600}$) measured by UV-vis spectroscopy (Cary100Bio) was 0.2 ($1.6 \times 10^8$ cell·$mL^{-1}$). Bacterial suspension was added (10 µL of $1.6 \times 10^8$ cell·$mL^{-1}$) into LB medium (1 mL) for each tube. LB medium was used as a control, different concentrations of (0.05 µg/mL, 0.5 µg/mL, 5 µg/mL) AuNC@lys capped kana-loaded MSN were added separately and shaken at 37° C. on a shaker at 240 rpm for 3, 6, and 9 h. The bacterial viability was determined by $OD_{600\ nm}$ using Novaspec™ Plus Visible Spectrophotometer. Each concentration was prepared and measured in triplicate.

Kinetics of antibacterial activity of MSN-AuNCs@lys. Bacterial suspension was added (10 µL of $1.6 \times 10^8$ CFU $mL^{-1}$) into LB broth (1 mL) for each tube. System free bacterial suspension was used as a control and 0.5 µg/mL of each system were added separately and shaken at 37° C. on a shaker at 240 rpm and the $OD_{600}$ was measured over 180 min. Then 10 µL of control, AuNCs@lys capped RhB-MSN and AuNCs@lys capped kana-MSN were plated on LB agar and incubated at 37° C. overnight to count the number of bacterial colonies.

Dual activity of AuNCs@lys and Kanamycin. To examine the effect of bacterial exposure on the fluorescence of AuNCs@lys and Kana release, E. coli (10 µL of $1.6 \times 10^8$ cell·$mL^{-1}$) was added to LB broth with different concentrations of (0.005 µg/mL, 0.05 µg/mL, 0.5 µg/mL, 5 µg/mL) kana MSN-AuNC@lys. The suspension was shaken and incubated at 37° C. over time. The change in fluorescence was measured by fluorometer and kana release was detected by UV-vis at absorbance $\lambda_{max}$ of 527 nm.

Pristine polymer coating. 3 wt % of PEO-PBT polymer was added and dissolved under reflux condition overnight. The resulting polymer solutions were transferred into a petri dish and evaporated at room temperature for 24 h. The thin film coating was then dried in a vacuum oven at 60° C. to remove the residual trace of water or THF.

Composite coating. About 20 mg/ml of AuNCs@lys capped kana-MSN was dispersed in DI water. 1 ml of the predetermined aqueous MSN solution was diluted by 4 ml of THF to make mixed solution with THF/DI water (80/20 wt %). Then to ensure a good dispersion the resulting solutions were sonicated for 1 h. To this, 3 wt % (150 mg) of PEO-PBT polymer was added and dissolved under reflux condition overnight. The same evaporation procedure of the pristine film was followed to obtain the composite coating.

Photo-Stimulable Phosphor (PSP) coating. The resulting composite solution was spin-coated on the PSP surface with controlled thickness. The coated PSP plate was then transferred to a vacuum oven to get rid of the residual water.

Live/dead assay. The AuNCs@lys capped kana-MSN membrane was completely immersed into a bacterial suspension (5 mL) in a sterile 15 mL conical tube. The membrane was incubated at room temperature for 8 hr. Live-dead assay was performed by immersing the membrane in the live/dead assay reagent, which was prepared according to the manufacturer. This was followed by two times washing with PBS. The membrane was mounted on a slide and imaged by laser scanning confocal microscope.

Cell culture. MCF-7 and HCT-116 cells were seeded at a density of $5 \times 10^3$ cells/well. Cells were cultured in EMEM medium containing 10% of FBS and 0.1% of penicillin-streptomycin at 37° C. in a humidified 5% $CO_2$ atmosphere. The media of MCF-7 was supplemented with 0.01 mg/mL.

MTT Assay. The cell viability was tested by the MTT (3-(4,5-dimethylthiazol-2-yl)-2,5 diphenyltetrazolium bromide, Life Technologies, Carlsbad, Calif., USA) assay following the manufacture's instruction. Briefly, MCF-7 and HCT-116 cells ($5 \times 10^3$ cells per well) were seeded onto a 96-well plate. On the following day, the culture medium was changed, and cells were incubated with different concentrations (200, 100, 50, 25, 12.5 and 6.25 µg/mL) of kanamycin loaded MSN-AuNCs@Lys in 200 µL of fresh medium at 37° C. for 24 h. After 24 h, the medium was discarded, and prepared culture medium containing 12 mM MTT solution was added into each well, including a negative control of culture media alone. After 3 h incubation, the medium was removed from the wells. Then 50 µL of DMSO was added to each well and mixed thoroughly for 10 min. The absorbance was measured at 540 nm using a microplate spectrophotometer (xMark™ Microplate Absorbance Spectrophotometer).

Material Characterization. The surface morphologies of the pure and composite membrane were investigated by field emission Scanning Electron Microscopy using SEM Quanta 600. Standard (TEM) images were collected using a Tecnai G2 Spirit TWIN 20-120 kV/LaB6. The NPs were dispersed in ethanol and drop casted on a lacy copper grid and dried for 1 h prior to analysis. The chemical composition of the NPs was measured by FTIR spectrometer in the range of 500 to 4000 $cm^{-1}$. The X-ray powder diffraction (XRD) patterns were obtained for NPs by a Bruker D8 Advance at a scanning rate of 1°/min in the 2θ range of 2-8°. X-ray photoelectron spectroscopy (XPS) was utilized to analyze the surface composition of the membrane film. The membrane topography and the quantitative surface roughness was measured by an Atomic Force Microscope (AFM) using Agilent 5400 SPM instrument (USA). BET surface area of the NPs were determined using surface area and porosimetry system "Micromeritics" (ASAP 2420) at 77 K.

Results and Discussion

Figure 7A:
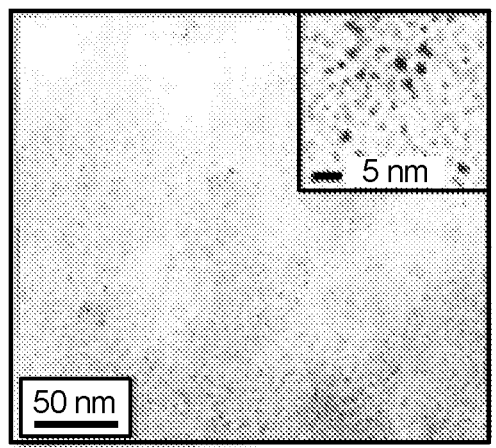
FIGS. 7(a)-(c) is a graphical view of (a) a TEM micrograph of AuNC@Lys (b) along with its fluorescence spectrum, and (c) zeta-potential over different pHs, according to one or more embodiments of the present disclosure.
Figure 7B:
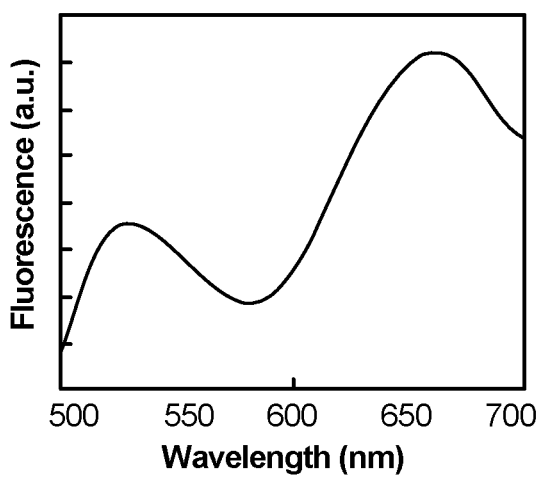
Figure 7C:
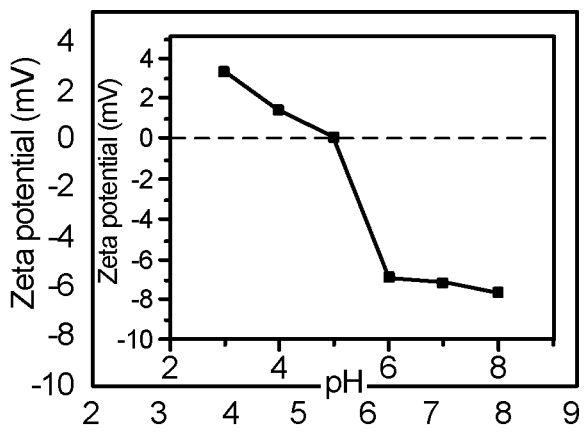

Characterization of MSN-AuNCs@lys. AuNCs are well known for their facile synthesis, red emission, and high quantum yield. AuNCs can be used as gatekeepers due to their strong electrostatic interaction with protonated amino groups as well as their high biocompatibility. AuNCs@lys were synthesized according to a previously published procedure. Briefly, aqueous HAuCl4 solution (10 mM, 5 mL) was added to lysozyme solution (50 mg/mL, 5 mL) at 37° C. under vigorous stirring for 10 min. Then, NaOH (1M, 0.5 mL) solution was introduced to the mixture and incubated at 37° C. for 12 h. The resulting AuNC@Lys (1 nm in diameter) was characterized by TEM and fluorometer (FIGS. 7(a)-(b)). Zeta potential confirmed that AuNC@Lys are negatively charged (FIG. 7(c)).

Figure 8:
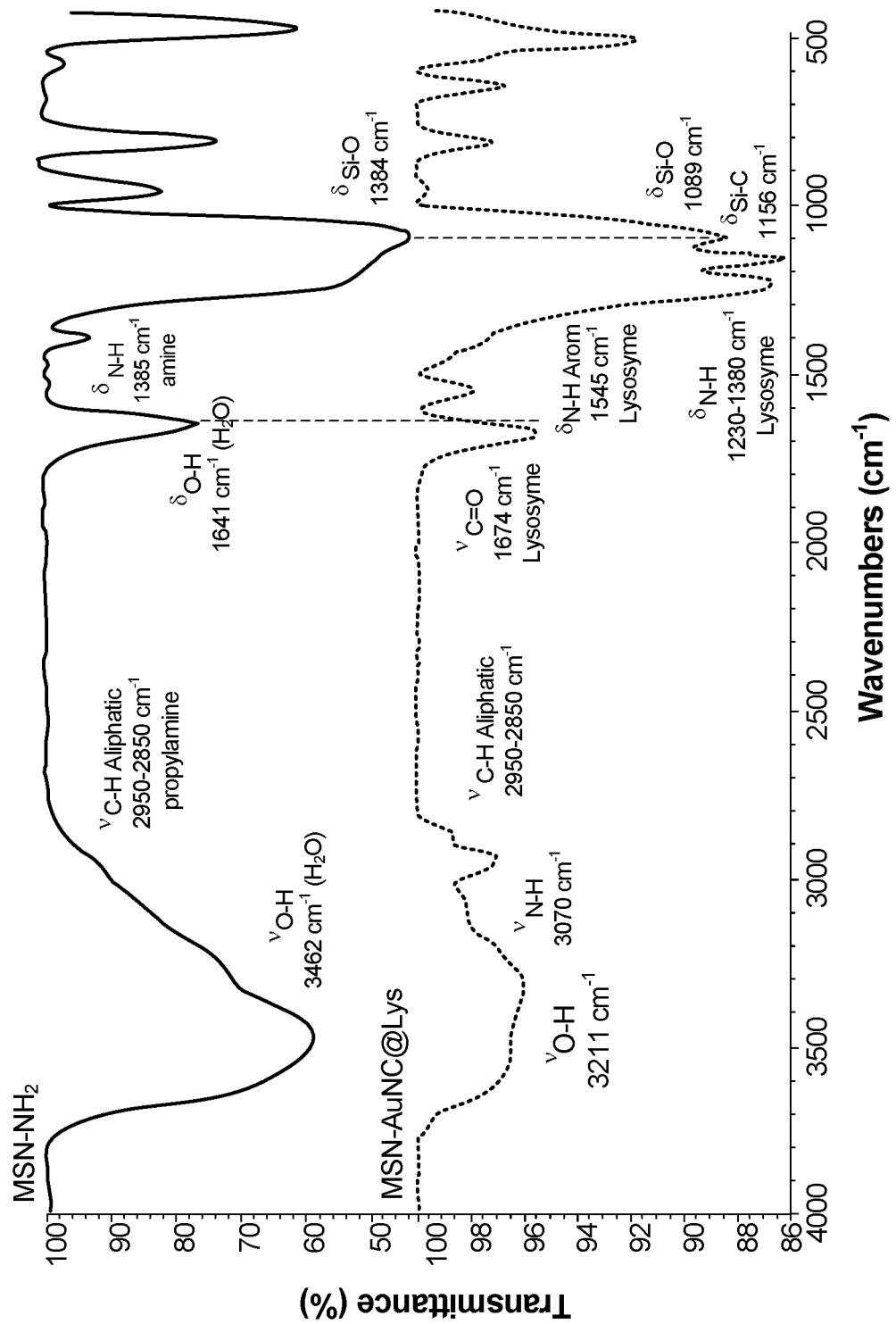
FIG. 8 is a graphical view of FTIR analyses of MSN-NH$_2$ and the resulting MSN-AuNC@Lys after pore capping confirming the presence of AuNC@Lys onto MSN, according to one or more embodiments of the present disclosure.

Biocompatible MCM-41 Si NPs were synthesized according to the reported sol-gel method with an average diameter of 120 nm. MSN surface functionalization was mediated by aminopropyltriethoxysilane (APTES), followed by CTAB extraction to obtain $NH_2$-MSN. The synthesis and treatment processes of the MSN have been characterized using TEM images, pattern, FTIR spectra and Thermogravimetric analysis (TGA). The infrared band at 1384 $cm^{-1}$ confirms $NH_2$ functionalization (FIG. 8).

Figure 9A:
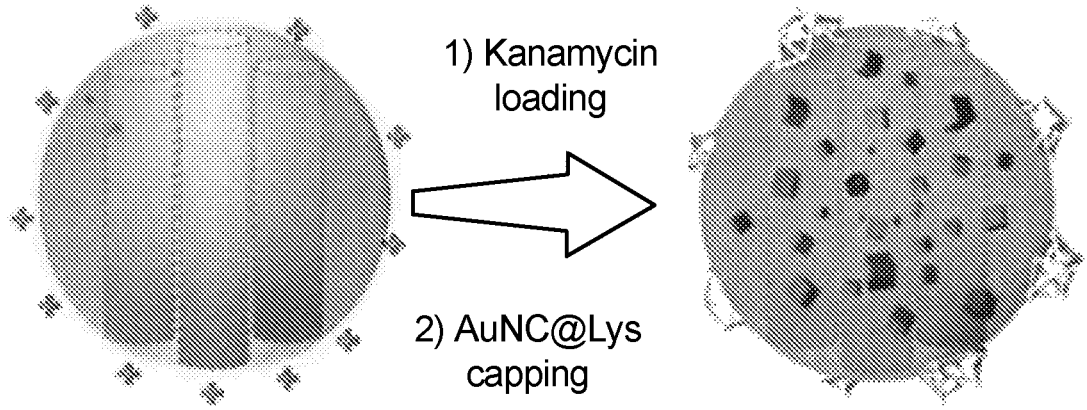
FIGS. 9(a)-(e) include (a) a schematic diagram of preparation of kanamycin-loaded MSN-AuNC@Lys; TEM micrographs (b) before and (c) after coating of MSN-NH$_2$; (d) XPS of kanamycin-loaded MSN-AuNC@Lys in the 4f gold region; and (e) nitrogen sorption of designed NPs, according to one or more embodiments of the present disclosure.
Figure 9B:
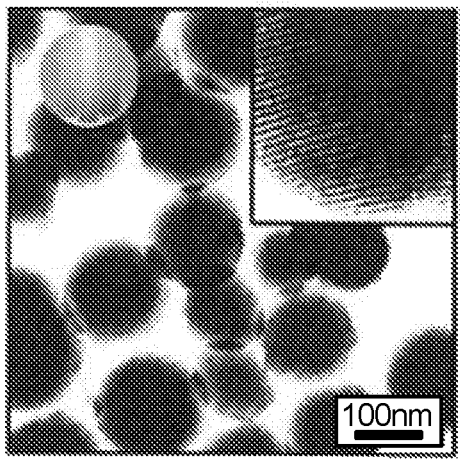
Figure 9C:
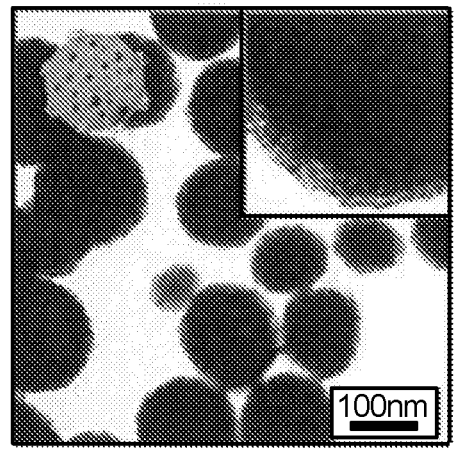
Figure 9D:
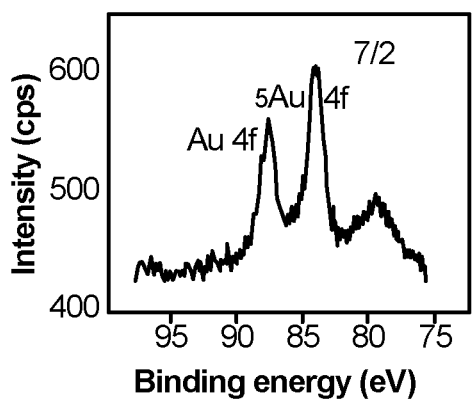
Figure 9E:
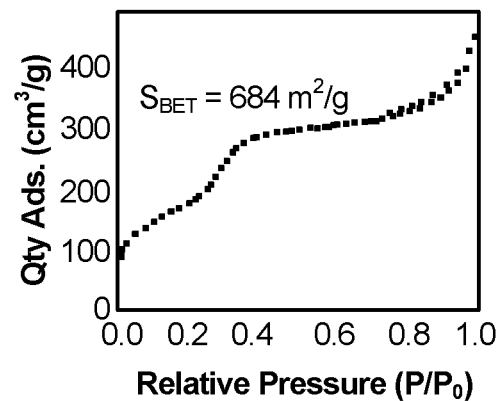
Figure 10A:
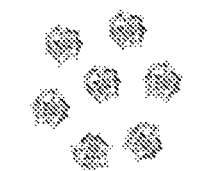
FIGS. 10(a)-(d) include schematic diagrams and photographs of (a) AuNC@Lys depicting the red emission of the clusters, (b) MSN before and after centrifugation depicting the white scattering of silica particles, (c) kanamycin-loaded MSN-AuNC@Lys depicting the slight red emission in an opaque solution from the cluster-coated silica NPs (kanamycin absorbs at 260 nm), and (d) rhodamine B-loaded (RhB-loaded) MSN-AuNC@Lys depicting the emission of rhodamine cargos (553 nm), according to one or more embodiments of the present disclosure.
Figure 10A:
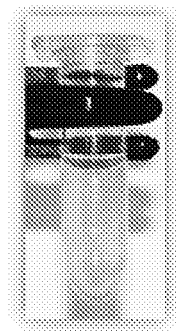
Figure 10B:
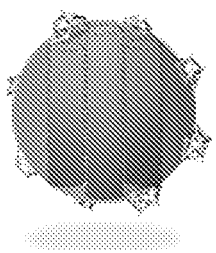
Figure 10B:
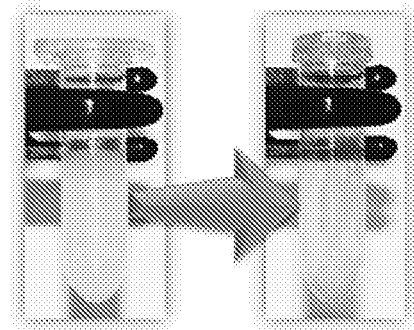
Figure 10C:
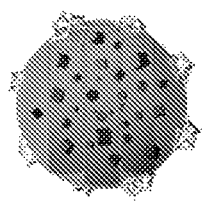
Figure 10C:
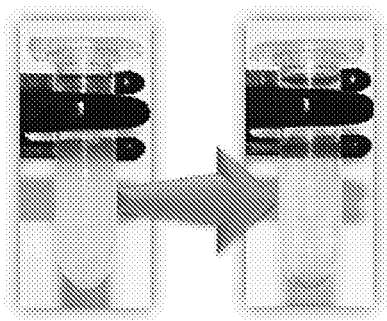
Figure 10D:
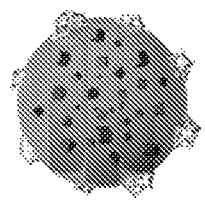
Figure 10D:
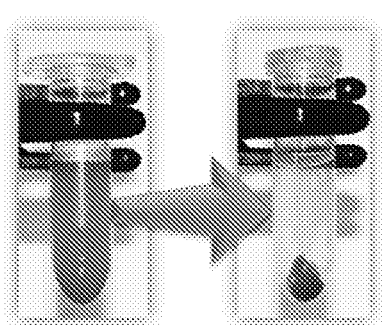

The MSN pores are big enough to load cargo molecules and small enough to be effectively capped by AuNCs@lys (FIG. 9(a)-(c)). TEM images show a clear difference in the surface morphology between MSN-$NH_2$ (FIG. 9(b)) and MSN-AuNC@Lys (FIG. 9(c)) supporting successful AuNC@Lys capping of MSN. This was further confirmed by FTIR analysis (FIG. 8) and high resolution XPS (FIG. 9(d)). The nanoparticles porosity was investigated by $N_2$-adsorption-desorption isotherms showing a high surface area of 684 $m^2g^{-1}$ (FIG. 9(e)). The Barret-Joyner-Halenda (BJH) method of calculation was employed to determine the pore size, which was calculated to be 2.3 nm. A bactericidal agent, kanamycin, was loaded inside $NH_2$-MSN in PBS at room temperature for 24 h followed by addition of negatively charged AuNCs@lys to trap the cargo in the pores electrostatically (FIG. 10(a)-(c)). RhB was also used as a control cargo to confirm the proper operation of the system by monitoring the fluorescence of this dye (FIG. 10(d)).

Figure 11A:
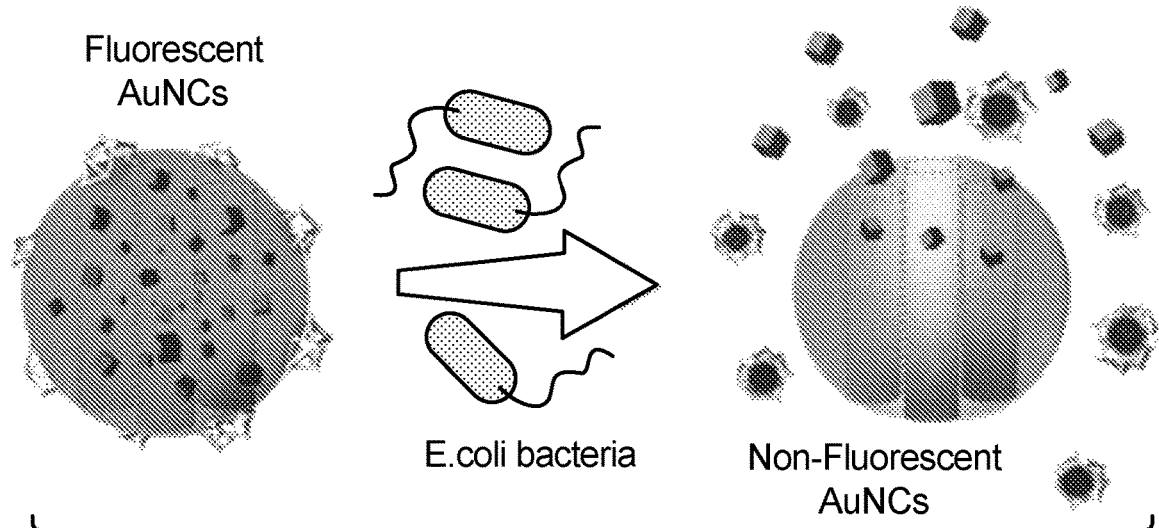
FIGS. 11(a)-(e) include (a) a schematic illustration of bacteria-triggered release from MSN-AuNCs@Lys NPs; (b) fluorescence emission spectra of AuNCs@Lys showing that, as the activity of lysozyme increases, the fluorescence of AuNCs decreases; (c) a release profile of RhB-loaded MSN-AuNCs@Lys showing no leakage or premature release; and kinetics of antibacterial activity of MSN-AuNCs@Lys loaded (d) RhB and (e) kanamycin (0.5 g/mL) in LB broth at initially fixed bacteria concentration, according to one or more embodiments of the present disclosure.
Figure 11B:
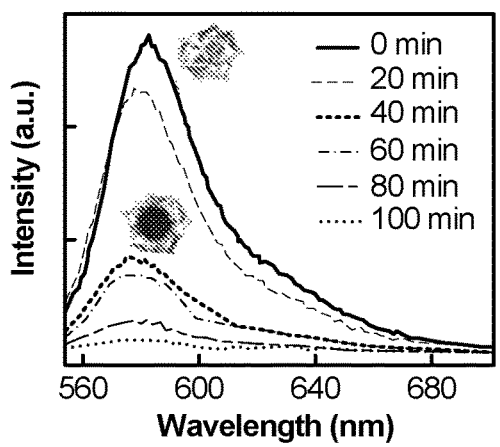
Figure 11C:
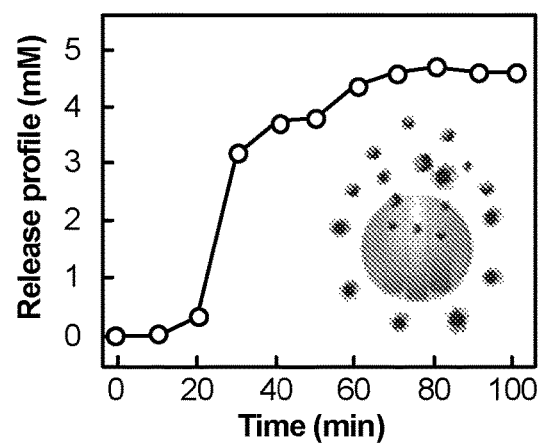

Antibacterial Activity of MSN-AuNCs@lys. The activity of AuNCs@lys and simultaneously the controlled release property of the system was then tested in the presence Escherichia coli (E. coli) (FIG. 11(a)). E. coli was selected as a model for studying the antibacterial activity of AuNCs @lys capped kanamycin-MSN, as it is well-characterized and medically relevant bacterium. As lysozyme initiates its degradation of the bacterial cell wall, the fluorescence of AuNCs quenches gradually (FIG. 11(b)). This reveals that the fluorescence of AuNCs strictly depends on the lysozyme catalytic activity. All antibacterial activity tests were performed in triplicates and were done at different times to ensure reproducibility. RhB was used as a model cargo to examine its controlled release from AuNCs@lys capped MSN in Luria broth (LB). RhB-MSN-AuNCs@lys were incubated with E. coli (1.6×10$^6$ cell·mL$^{-1}$) at 37° C. under gentle shaking. This dynamic contact assay resulted in the release of 4.25 mM of RhB from MSN (FIG. 11(c)) with zero leakage.

Figure 11D:
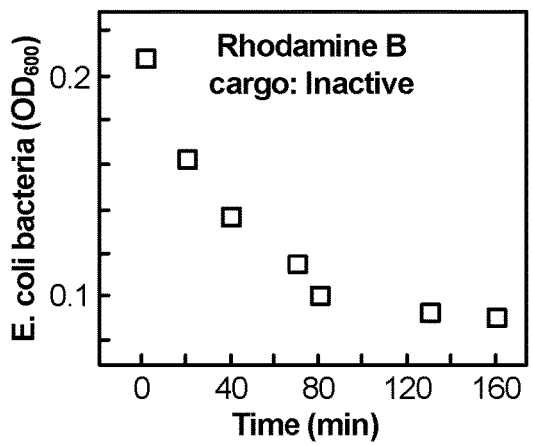
Figure 11E:
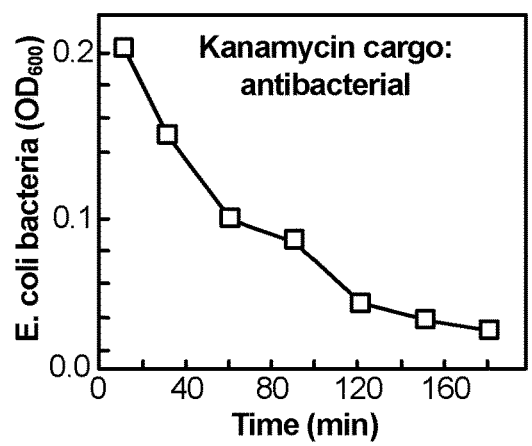
Figure 12A:
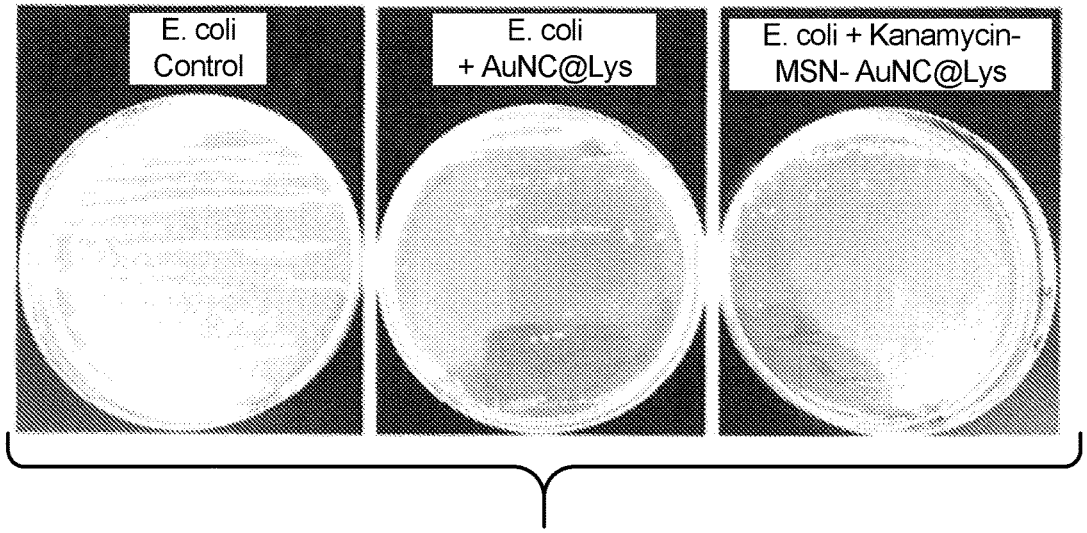
FIGS. 12(a)-(c) show (a) images illustrating the antimicrobial activity of kanamycin MSN-AuNCs@Lys against E. coli, where a portion of the LB broth bacterial suspension was streaked on LB agar and system free E. coli was used as a control to compare the bacterial growth; (b) the antibacterial activity of different concentrations over time towards E. coli; and (c) the release of kanamycin from loaded MSN-AuNCs@Lys, where the release was done by incubating the system with E. coli in LB broth solution over time (calculated by correlating the amount of released kanamycin to the control (free kanamycin 0.1 mg/mL), according to one or more embodiments of the present disclosure.
Figure 12B:
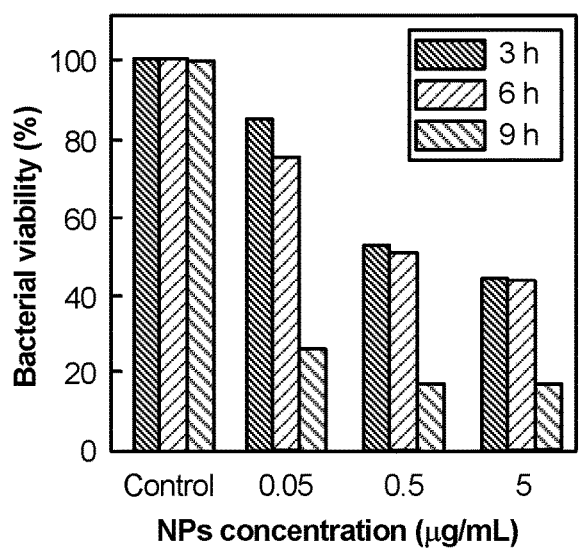
Figure 12C:
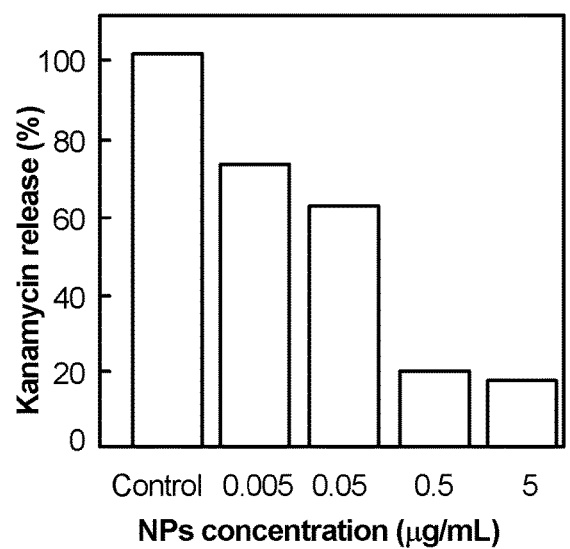

E. coli Inhibition Kinetics. E. coli inhibition kinetics in response to its interaction with AuNCs@lys (0.5 µg/mL) capped RhB-MSN (FIG. 11(d)) and Kanamycin-MSN (FIG. 11(e)) were studied over 3 h. The antibacterial activity here was related to the activity of AuNCs@lys. Compared to the control point (OD$_{600}$: 0.2), E. coli viability was decreased by 50% in 80 min due to the activity of AuNCs@lys when an inactive control cargo such as RhB was used (FIG. 11(d)). While incorporating an active ingredient in the pore such as kanamycin decreased the viability by 50% in just 60 min (FIG. 11(e)). Examining the stimuli responsive release of kanamycin to refine the study, a total of 100 µg/mL of kanamycin was loaded in MSN. Dynamic contact assay was used to determine the efficacy of antibacterial activity of AuNCs@lys capped kanamycin-MSN (FIG. 12(a)). Different concentrations of AuNCs@lys capped kanamycin-MSN (0.05 µg/mL, 0.5 µg/mL and 5 µg/mL) were incubated with E. coli (1.6×10$^6$ cell·mL$^{-1}$) at 37° C. under gentle shaking in LB broth for up to 9 h. A system free bacteria was used as a positive control. As shown in FIG. 12(b), AuNCs@lys capped kanamycin-MSN were able to inhibit the growth of E. coli by more than 80% at a concentration of 5 µg/mL over a short period of time. Kanamycin release was detected at absorbance $\lambda_{max}$ of 527 nm and free kanamycin (0.1 mg/mL) was used as a positive control. The amount of kanamycin released was also studied relating to the same initial bacterial density (FIG. 12(c)). At high system/lysozyme concentration (5 µg/mL), only 18% of kanamycin was needed to kill E. coli. The rest of kanamycin was trapped within the MSN, as AuNCs@lys are intact and still capping the pores of MSN. On the other hand, 73% of the kanamycin was released at a low system concentration (0.005 µg/mL) as the amount of lysozyme was not sufficient to kill the same bacterial density, verifing the on-demand activation and release of the designed system (FIG. 12(c)).

Figure 13:
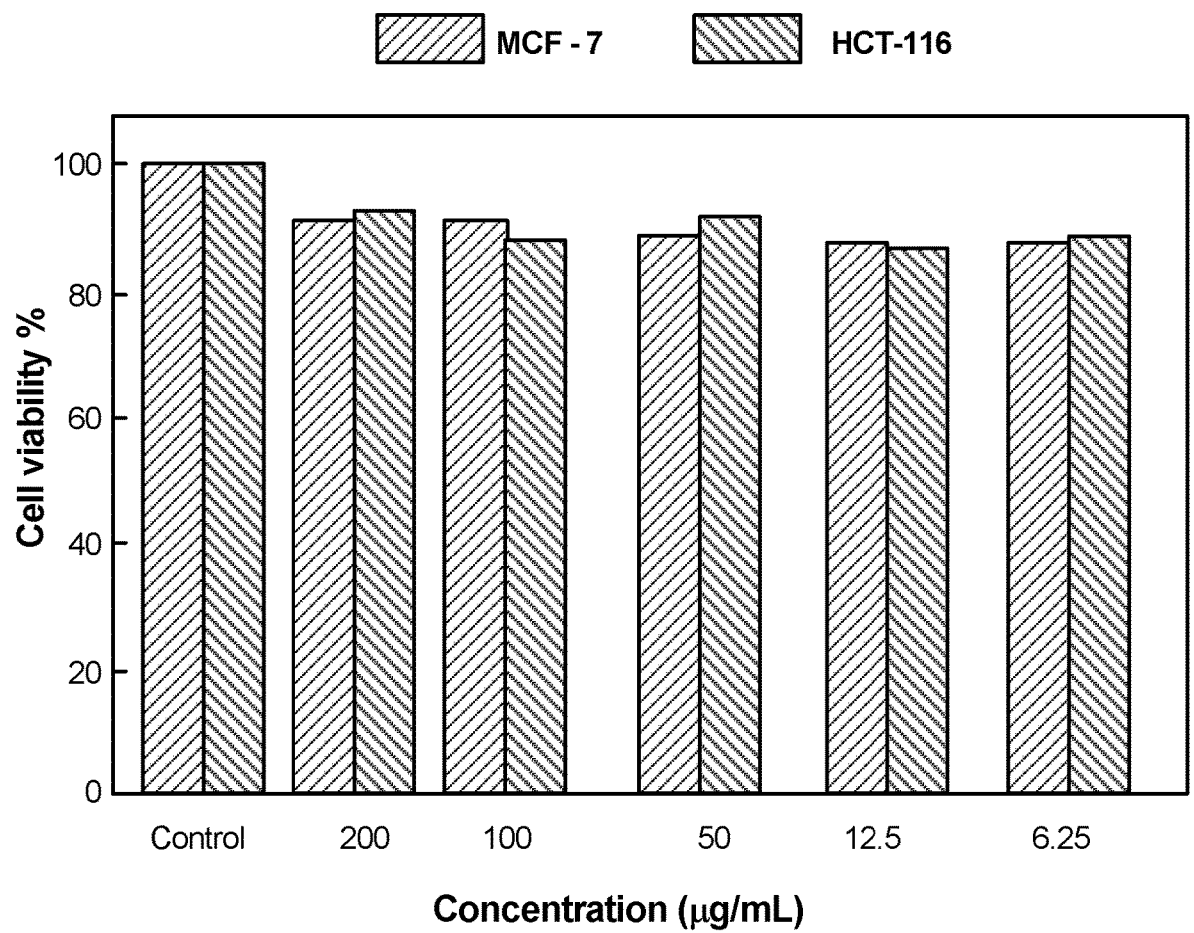
FIG. 13 is a graphical view showing in vitro biocompatibility, where cell viability was measured by the 3-(4,5-dimethylthiazol-2-yl)-2,5 diphenyltetrazolium bromide (MTT) after transfection; where MCF-7 and HCT-116 cells were plated on a 96-well plate and treated with different concentrations of kanamycin loaded MSN-AuNCs@Lys for 24 h; and where the results are presented as the mean of three determinations, according to one or more embodiments of the present disclosure.

Biocompatibility of MSN-AuNCs@lys. AuNCs@lys capped kanamycin-MSN biocompatibility was tested in two different cell lines MCF-7 and HCT-116. Their cytotoxicity was assessed by the 3-(4,5-dimethylthiazol-2-yl)-2,5 diphenyltetrazolium bromide (MTT) assay and results were compared to the controls. The data obtained proves that the NPs are biocompatible even at high concentration (200 µg/mL) (FIG. 13).

Figure 14A:
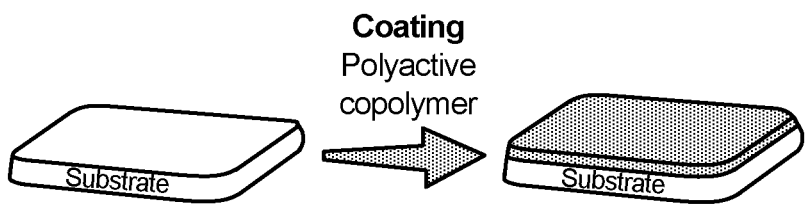
FIGS. 14(a)-(i) include schematic diagrams and/or images of a polymer coating (a) without and (b) with antibacterial NPs along with corresponding (c,d) SEM and (e,f) AFM micrographs showing that the roughness (R) observed on the membrane by AFM have different scales and supports the higher roughness of the NPs-doped polyactive membrane; (g) the cross section; (h) SEM; and (i) TEM micrographs of the cut membrane reveal the successful incorporation and uniform dispersion of mesoporous NPs, according to one or more embodiments of the present disclosure.
Figure 14B:
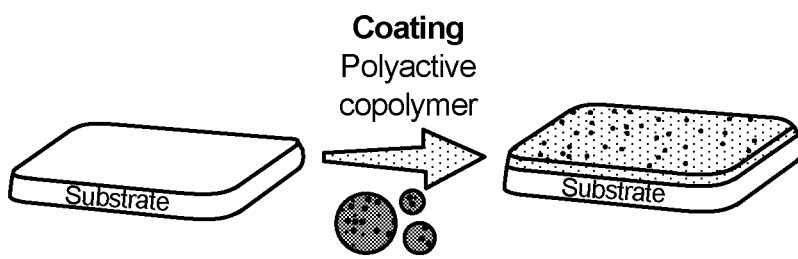
Figure 14C:
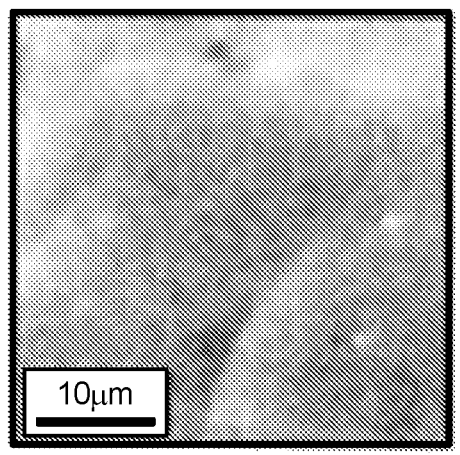
Figure 14D:
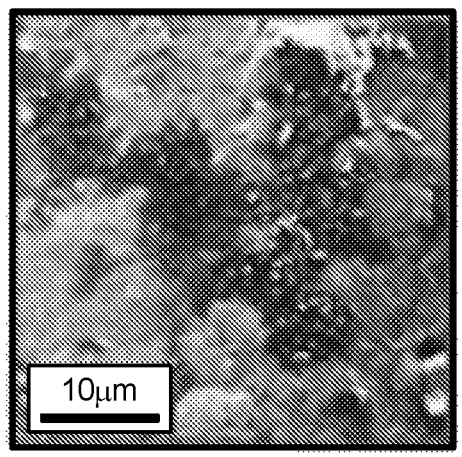
Figure 14E:
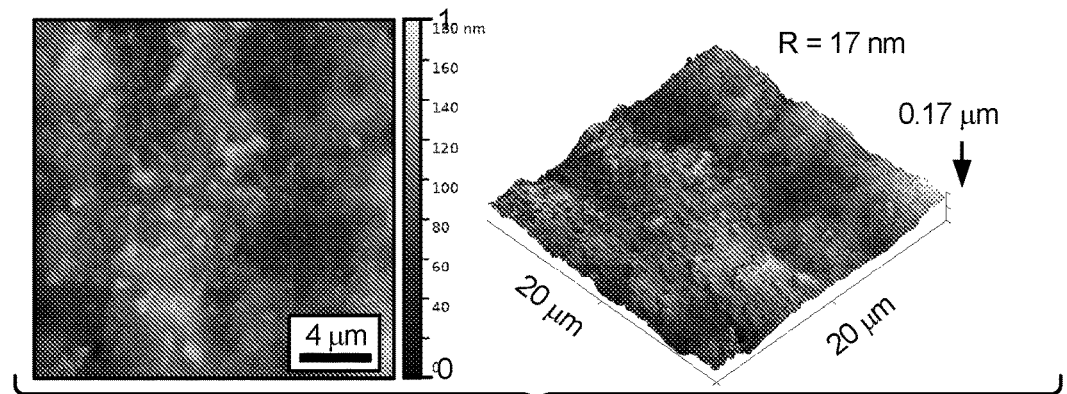
Figure 14F:
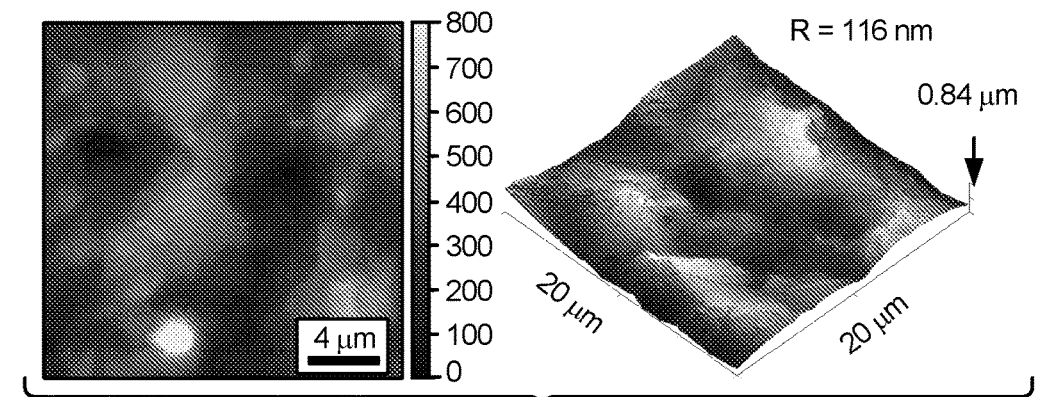
Figures 14G, 14H:
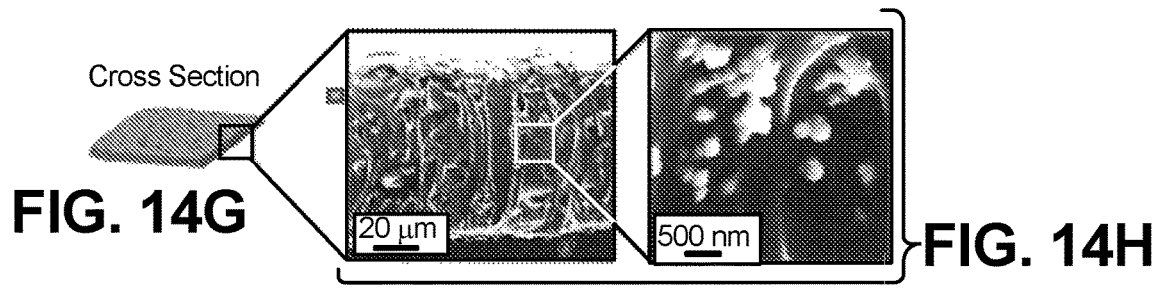
Figure 14I:
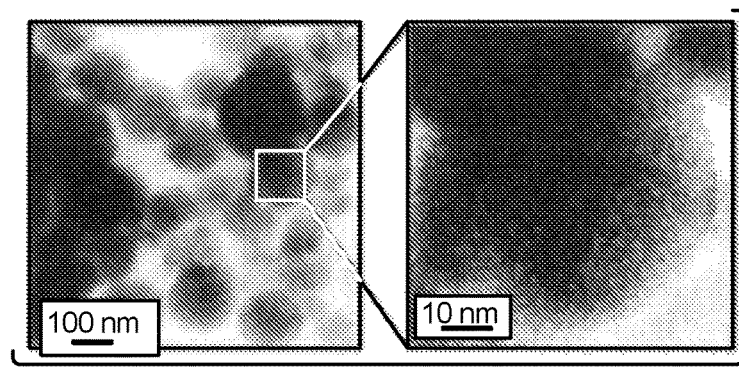

Mixed Matrix Coating based on MSN-AuNCs@lys. The antibacterial MSN-AuNCs@lys nano-fillers were then mixed with PEO/PBT copolymer (Polyactive). PolyActive is a promising polymer for manufacturing membranes. It is flexible, environmentally friendly, biocompatible, and cost-effective. This amphiphilic copolymer is soluble in tetrahydrofuran (THF), therefore, it is miscible with water. This allowed mixing of the aqueous dispersed NPs with the polymer solution without any phase separation or precipitation of the polymer during NPs addition. Thin films (50 µm) were fabricated employing PEO-PBT suspension and 10% wt of MSN-AuNCs@lys NPs, which showed a very good dispersion in THF/DI water mixture (80/20%). The thin film coating was prepared by slow evaporation of the solvent at room temperature (FIG. 14(a),(b)). SEM images show a uniform structure of the pristine polymer coating (FIG. 14(c)). However, a spiked rough structure appeared on the top surface of the composite membrane containing MSN-AuNCs@lys NPs (FIG. 14(d)). Surface roughness significantly increases from 16.69 to 115.98 nm, which was detected by AFM (FIG. 14(e),(f)). This increase in roughness may also aid NPs to attach strongly to bacteria so they efficiently destroy the cell well by the action of lysozyme. SEM cross-section shows that NPs were uniformly dispersed in the polymer matrix with intact porosity (FIG.

Figure 15:
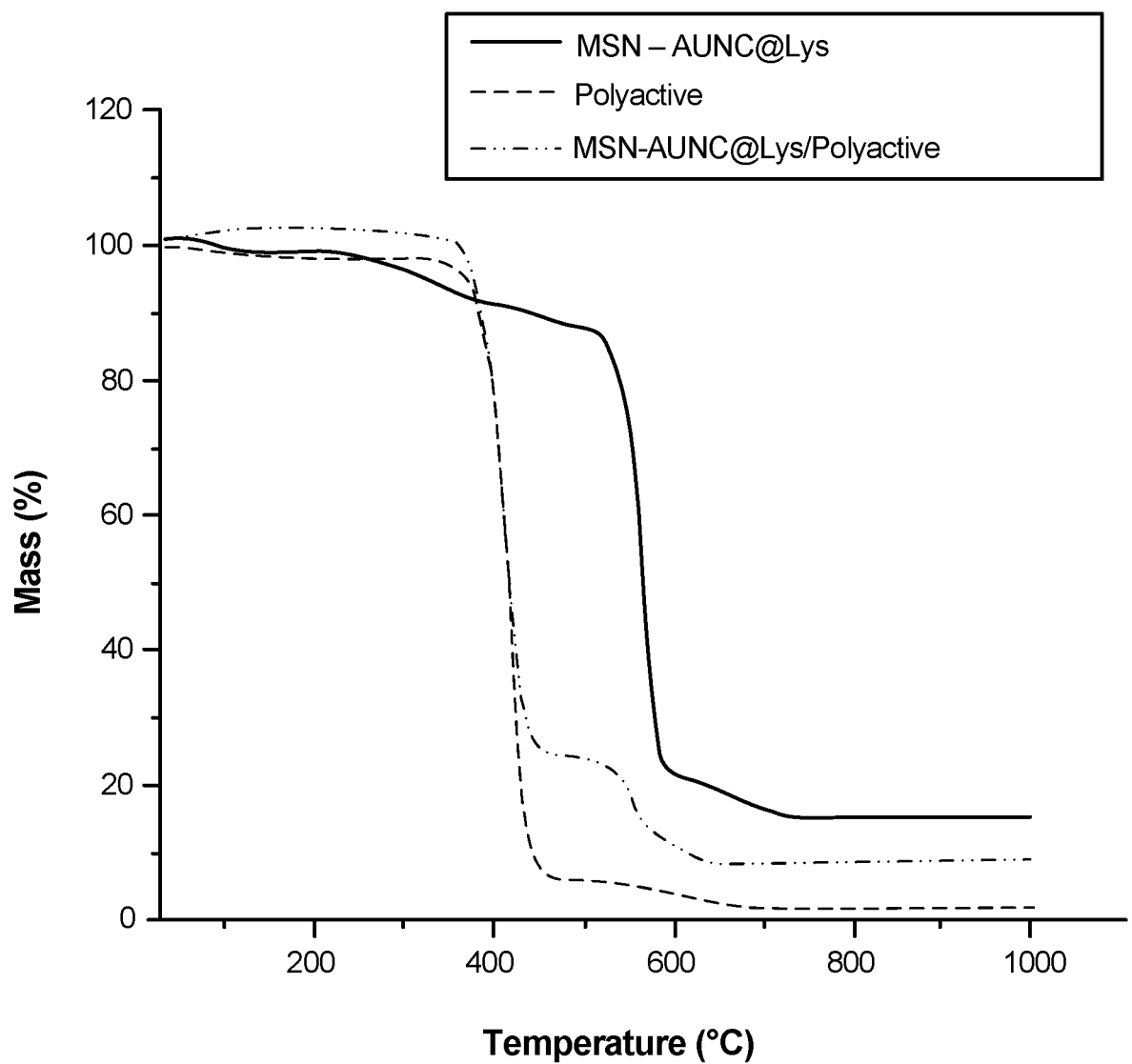
FIG. 15 is a graphical view of TGA analyses of MSN-AuNC@Lys, polyactive membrane, and the membrane nanocomposites confirming the incorporation of MSN-AuNC@Lys into the polyactive, according to one or more embodiments of the present disclosure.

14(g)-(i)). TGA analysis of the composite membrane confirms its thermal stability and verifies NPs incorporation (FIG. 15).

Figure 16A:
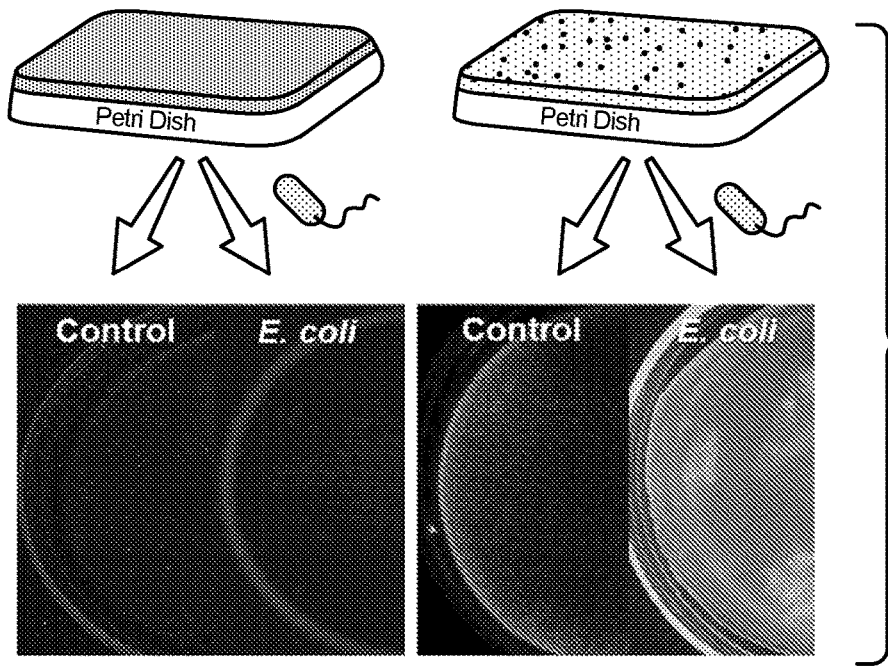
FIGS. 16(a)-(c) include (a) a schematic diagram and images of the membrane immersed in E. coli containing broth and showing that AuNCs fluorescence quenched upon the exposure to E. coli; (b,c) images of CLSM of E. coli stained with fluorescent cell viability marker (live/dead) assay), where viable bacteria appear as green dots and non-viable bacteria appear as red dots, with (b) showing that, in the presence of uncoated membrane, live bacteria dominated as shown from the calcein stained green dots and (c) showing that all of E. coli are dead as shown in the EtBr stained red dots when a coated PSP plate was used, according to one or more embodiments of the present disclosure.
Figure 16B:
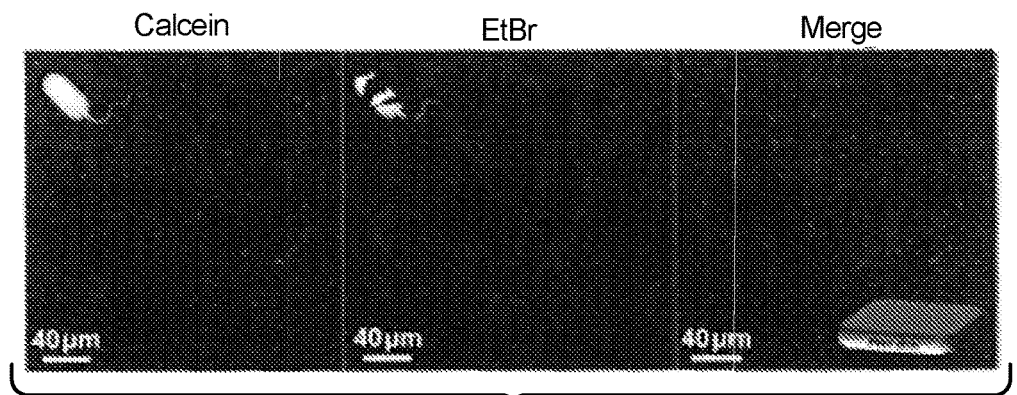
Figure 16C:
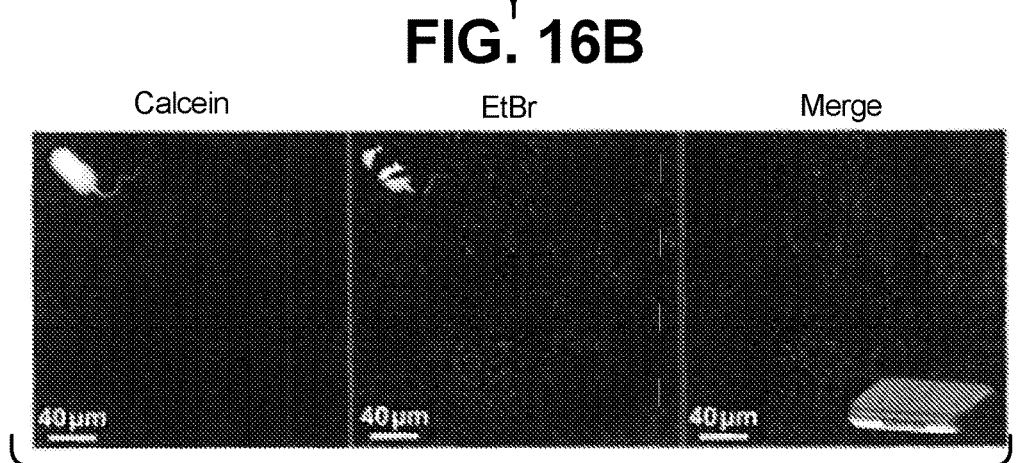

Antibacterial Activity of the Mixed Matrix Membrane. *E. coli* (3 mL, $OD_{600}$: 0.6) was then poured on the membrane and left for 8 h. As shown in FIG. 16(a), the fluorescence of AuNCs@lys was sharply quenched, indicating lysozyme activity and kanamycin release. Live-dead assay corroborated findings where viable bacteria is stained in green and dead bacteria is stained in red (FIG. 16(b),(c)). Using only polyactive membranes, most of the bacteria remained viable as shown with green calcein (FIG. 16(b)). Employing MSN-AuNCs@lys mixed matrix coating, all bacteria was dead as shown with red EtBr (FIG. 16(c)). This rapid bacterial action prevented bacterial accumulation on surfaces and eventual biofilm formation.

Figure 17A:
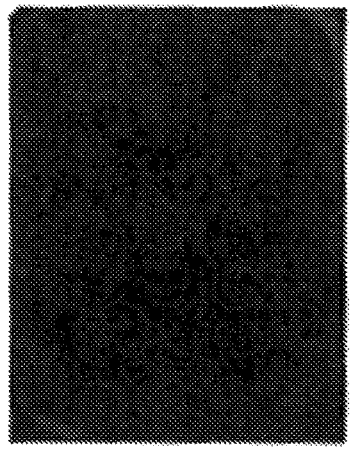
FIGS. 17(a)-(e) includes photographic images of antibacterial mixed matrix membrane coated PSP Dental plate under UV light, with (a) showing no bacterial contamination (red fluorescence intact); (b) showing low bacterial contamination where the controlled release antimicrobial action of the NPs nanofillers inhibited the growth as supported by the decrease in red fluorescence; (c) showing high bacterial contamination as flagged by the complete disappearance of red fluorescence; and also including X-ray radiographic dental images using (d) uncoated and (e) antibacterial-coated PSP plate under the same operational conditions, demonstrating that the coated plate can provide high resolution images that are similar to the quality of images obtained with uncoated plates, according to one or more embodiments of the present disclosure.
Figure 17B:
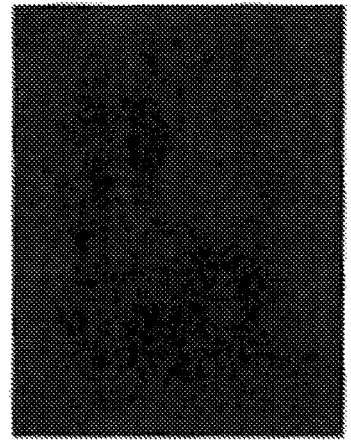
Figure 17C:
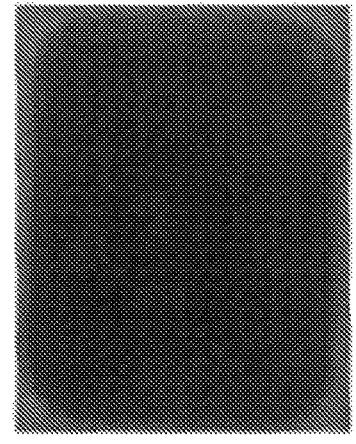
Figure 17D:
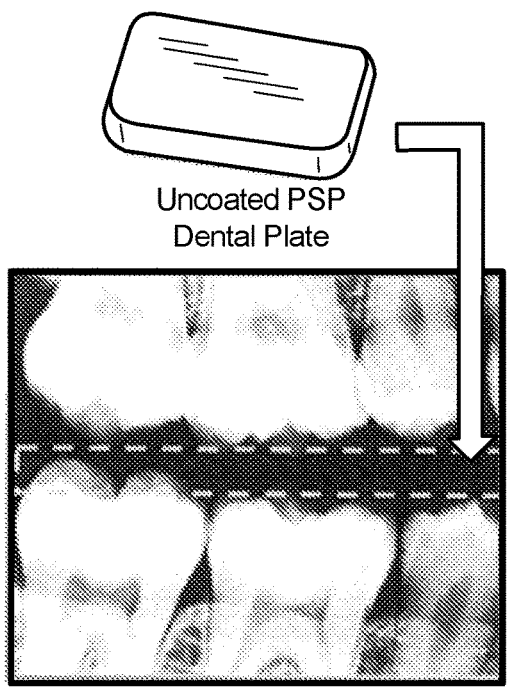
Figure 17E:
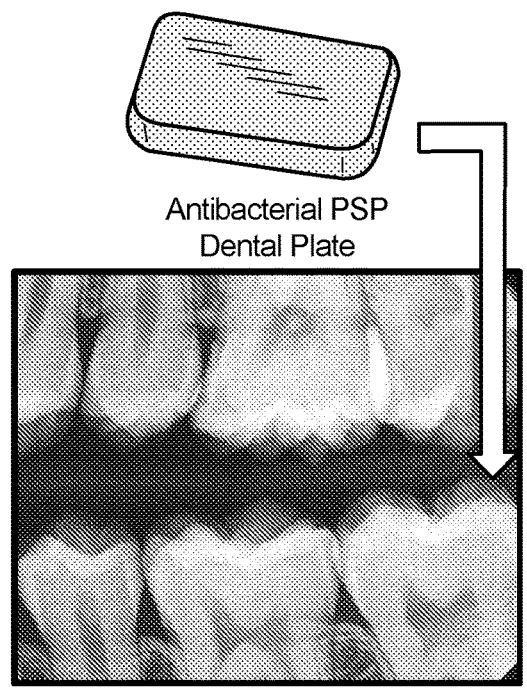

Coating X-Ray Dental Imaging Plates. To examine the effectiveness of the membrane as antibacterial coating, a Photo-Stimulable Phosphor (PSP) plate was coated with the developed membrane. These imaging plates were used to capture and store a latent radiographic image. The PSP plate is usually inserted into a plastic sleeve, or "barrier envelope," prior to insertion into the patient's mouth. A major limitation of PSP plates is the possibility of transferring contaminated material to patient's mouth if integrity of plate's protective envelope is jeopardized. Coating the PSP plate with MSN-AuNCs@lys mixed matrix coating showed a bright red color in the absence of bacterial contamination (FIG. 17(a)). At low bacterial contamination ($5 \times 10^3$ cell·mL$^{-1}$), the antibacterial nanofillers could quickly inhibit the bacterial infection and a decrease in red fluorescence is observed (FIG. 17(b)). However, only a blue color was obtained in case of high bacterial contamination as shown in FIG. 17(c). Most importantly, the designed mixed matrix coating did not jeopardize the quality of the dental images obtained with these plates. FIG. 17(d) shows actual dental images obtained by non-coated plates while FIG. 17(e) shows an image taken with the mixed matrix coated plate at the same operating conditions. The designed coating did not compromise the quality of the images obtained and at the same time is safer for practical use.

In sum, a dual-functional sensing and controlled release antibacterial smart coating is described. This platform was based on protein-templated colloidal gold nanoclusters gating antimicrobial agent loaded mesoporous silica nanoparticles. These NPs acted as bacteria-responsive nano-fillers when incorporated in polyactive amphiphilic matrix to produce a homogenous mixed matrix membrane with no phase separation and zero leaching. The system selectively sensed and inhibited bacterial contamination through the synergistic effect of lysozyme and kanamycin. The absence of surface fluorescence showing blue color under UV light signaled bacterial contamination, while red fluorescent surfaces signaled bacteria-free environment. To support the practical utility of this coating, it was used to coat X-ray dental imaging plates as they are prone to oral bacteria contamination. The mixed matrix membrane was coated on a PSP plate and showed reproducible sensitivity as well as inhibition of bacterial growth. The quality of the images obtained with the coated plate were identical to the uncoated ones, proving the promising real-life applicability of this system. Moreover, this strategy can be expanded to include monitoring and inhibition of bacterial contamination on hospital surfaces, medical equipment, and other radiographic patient care devices.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A conjugate, comprising
a mesoporous nanoparticle having a plurality of pores, wherein the mesoporous nanoparticle is positively charged, wherein an active agent is disposed in the pore;
a plurality of metal nanoclusters, wherein the metal nanocluster has a negative charge, wherein a gate agent is lysozyme and the lysozyme is attached to the metal nanocluster;
wherein an electrostatic interaction causes the metal nanoclusters to seal in the active agent in the pore, wherein the gate agent is positioned on the outside surface of the conjugate so that it interacts with a gate target, wherein the active agent moves out of the pore upon removal of the metal nanocluster.

2. The conjugate of claim 1, wherein the mesoporous nanoparticle is a mesoporous silicon nanoparticle.

3. The conjugate of claim 1, wherein the active agent is selected from the group consisting of: an antimicrobial agent, anti-corrosion agent, antioxidant agent, antiscalant agent, and a combination thereof.

4. The conjugate of claim 3, wherein the antimicrobial agent is an antibacterial agent.

5. The conjugate of claim 4, wherein the antibacterial agent is kanamycin.

6. The conjugate of claim 1, wherein the metal nanocluster is a gold nanocluster.

7. A method of using a conjugate, comprising:
exposing a conjugate to microbes, the conjugate comprising:
an active agent disposed in a plurality of pores of a mesoporous nanoparticle, wherein the mesoporous nanoparticle is positively charged;
a plurality of metal nanoclusters having a negative charge and sealing in the active agent via an electrostatic interaction; and
a gate agent attached to the metal nanoclusters and positioned on an outside of the conjugate, wherein the gate agent is lysozyme;
wherein the gate agent interacts with a gate target sufficient to remove the metal nanocluster from the mesoporous nanoparticle and release the active agent; and
treating the microbes with the released active agent.

8. The method of claim 7, wherein the conjugate is included in a polymer coating on a surface of a substrate.

9. The method of claim 8, wherein the polymer is poly(ethylene oxide)/poly(butylene terephthalate).

10. The method of claim 7, wherein the active agent is an antibacterial agent.

11. The method of claim 7, wherein the mesoporous nanoparticle is one or more of a mesoporous silica nanoparticle, a mesoporous titania, a mesoporous carbon, metal-organic framework, and zeolite.

12. The method of claim 7, wherein the metal nanocluster includes one or more of a gold nanocluster, silver nanocluster, or copper nanocluster.

13. The method of claim 7, wherein the gate target is a cell wall of the microbe.

14. The method of claim 7, further comprising detecting a presence of a microbe.

15. The method of claim 7, wherein detecting includes one or more of measuring a fluorescence signal and observing a decrease in fluorescence.

16. The method of claim 15, wherein the fluorescence of the conjugate decreases upon exposing the conjugate to microbes.

17. A method of using a conjugate, comprising:
exposing a conjugate to microbes, the conjugate comprising:
an active agent disposed in a plurality of pores of a mesoporous nanoparticle, wherein the mesoporous nanoparticle is positively charged;
a plurality of metal nanoclusters having a negative charge and sealing in the active agent via an electrostatic interaction; and
a gate agent attached to the metal nanoclusters and positioned on an outside of the conjugate, wherein the gate agent is lysozyme; and
detecting a presence of the microbes.

18. The method of claim 17, wherein detecting includes one or more of measuring a fluorescence signal and observing a decrease in fluorescence.

* * * * *